US010575528B2

(12) United States Patent
Takanohashi et al.

(10) Patent No.: US 10,575,528 B2
(45) Date of Patent: Mar. 3, 2020

(54) PLANT DISEASE CONTROL COMPOSITION AND PLANT DISEASE CONTROL METHOD

(71) Applicant: SUMITOMO CHEMICAL COMPANY, LIMITED, Tokyo (JP)

(72) Inventors: Fumina Takanohashi, Tokyo (JP); Ayako Hirao, Tokyo (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 15/747,513

(22) PCT Filed: Jul. 27, 2016

(86) PCT No.: PCT/JP2016/072075
§ 371 (c)(1),
(2) Date: Jan. 25, 2018

(87) PCT Pub. No.: WO2017/018466
PCT Pub. Date: Feb. 2, 2017

(65) Prior Publication Data
US 2018/0220657 A1    Aug. 9, 2018

(30) Foreign Application Priority Data

Jul. 27, 2015 (JP) ................. 2015-147702
Dec. 22, 2015 (JP) ................. 2015-250259

(51) Int. Cl.
| | | |
|---|---|---|
| *A01N 63/00* | (2020.01) | |
| *A01N 37/50* | (2006.01) | |
| *A01N 43/40* | (2006.01) | |
| *A01N 43/54* | (2006.01) | |
| *A01N 47/24* | (2006.01) | |
| *A01N 43/88* | (2006.01) | |
| *A01N 37/38* | (2006.01) | |
| *C12N 1/20* | (2006.01) | |
| *A01C 1/08* | (2006.01) | |
| *A01N 37/36* | (2006.01) | |
| *C12R 1/07* | (2006.01) | |

(52) U.S. Cl.
CPC .............. *A01N 63/00* (2013.01); *A01C 1/08* (2013.01); *A01N 37/36* (2013.01); *A01N 37/50* (2013.01); *A01N 43/40* (2013.01); *A01N 43/54* (2013.01); *A01N 43/88* (2013.01); *A01N 47/24* (2013.01); *C12N 1/20* (2013.01); *C12R 1/07* (2013.01)

(58) Field of Classification Search
CPC combination set(s) only.
See application file for complete search history.

(56) References Cited

U.S. PATENT DOCUMENTS 6,995,007 B2    2/2006  Gunner et al.
7,666,406 B2    2/2010  Gunner et al.
2011/0110906 A1  5/2011  Andersch
2015/0282483 A1 10/2015  Sawada et al.
2017/0188584 A1* 7/2017  Jabs ................. A01N 63/02

FOREIGN PATENT DOCUMENTS

| JP | 10-109913 A | 4/1998 |
|---|---|---|
| JP | 2006-347885 A | 12/2006 |
| JP | 2011-519824 A | 7/2011 |
| JP | 2015-519352 A | 12/2013 |
| JP | 2014-139223 A | 7/2014 |
| JP | 2015-504905 A | 2/2015 |
| JP | 2016-155862 A | 9/2016 |
| WO | WO 03/055303 A1 | 7/2003 |
| WO | WO 2009/037242 A2 | 3/2009 |
| WO | WO 2011/162397 A1 | 12/2011 |
| WO | WO 2013/110591 A1 | 8/2013 |
| WO | WO 2013/178661 A1 | 12/2013 |
| WO | WO 2014/083033 A1 | 6/2014 |
| WO | WO 2015/004260 A1 | 1/2015 |

OTHER PUBLICATIONS

Bartlett, D.W. et al., "The strobilurin fungicides," Pest Management Science, vol. 58, pp. 649-662 (2002).*
Derwent abstract 2007-050901; abstracting JP 2006/347885 (dated Dec. 2006).*
International Preliminary Report on Patentability and English translation of the Written Opinion of the International Searching Authority (PCT/IB/373 and PCT/ISA/237) for International Application No. PCT/JP2016/072073, dated Jan. 30, 2018.
International Preliminary Report on Patentability and English translation of the Written Opinion of the International Searching Authority (PCT/IB/373 and PCT/ISA/237) for International Application No. PCT/JP2016/072074, dated Jan. 30, 2018.
International Preliminary Report on Patentability and English translation of the Written Opinion of the International Searching Authority (PCT/IB/373 and PCT/ISA/237) for International Application No. PCT/JP2016/072076, dated Jan. 30, 2018.
International Search Report (PCT/ISA/210) for International Application No. PCT/JP2016/072073, dated Sep. 13, 2016.
International Search Report (PCT/ISA/210) for International Application No. PCT/JP2016/072074, dated Sep. 13, 2016.
International Search Report (PCT/ISA/210) for International Application No. PCT/JP2016/072076, dated Sep. 13, 2016.
MacBean (Ed.), "The Pesticide Manual," A World Compendium, Sixteenth Edition, BCPC, 2012, pp. 97, 117-118, 122-123, 528-529, 559-560, 577, 671-672, 863-865, 868-869, 1021-1022, 1216 (27 pages total).

(Continued)

*Primary Examiner* — John Pak
(74) *Attorney, Agent, or Firm* — Birch, Stewart, Kolasch & Birch, LLP

(57) ABSTRACT

The present invention addresses the problem of providing a composition that has excellent plant disease controlling effects and provides a plant disease control composition that includes a new strain of *Bacillus*, APM-1 (New strain of *Bacillus*, APM-1), which has been deposited under ATCC Accession No. PTA-4838, and one or more ubiquinol oxidase Qo site inhibitor.

8 Claims, No Drawings

(56) References Cited

OTHER PUBLICATIONS

International Preliminary Report on Patentability and English translation of the Written Opinion of the International Searching Authority (PCT/IB/373 and PCT/ISA/237) for International Application No. PCT/JP2016/072072, dated Jan. 30, 2018.
International Preliminary Report on Patentability and English translation of the Written Opinion of the International Searching Authority (PCT/IB/373 and PCT/ISA/237) for International Application No. PCT/JP2016/072075, dated Jan. 30, 2018.
International Search Report (PCT/ISA/210) for International Application No. PCT/JP2016/072072, dated Sep. 13, 2016.
International Search Report (PCT/ISA/210) for International Application No. PCT/JP2016/072075, dated Sep. 13, 2016.
Peachey et al., "Mesiterpro Crop Protection Handbook," 2014 Centennial Edition, 2014, pp. 9, 191, 318-319, 358-360, 568-569.
The Insecticide Resistance Action Committee, "Mode of Action Classification," Insecticide Resistance Management, Fourth Edition, Dec. 2014, pp. 7, 20 (4 pages total).
U.S. Office Action for U.S. Appl. No. 15/746,551, dated Jul. 3, 2018.
U.S. Office Action for U.S. Appl. No. 15/747,699, dated Oct. 2, 2018.
EPA, "Pesticide Fact Sheet: Ipconazole," Sep. 2004, pp. 1-17.
Hilber et al., "Comparative resistance patterns of fludioxonil and vinclozolin in Botryotinia fuckeliana," Journal of Phytopathology, vol. 143, No. 7, 1995, pp. 423-438 (1 page, only abstract provided).
Kim et al., "Ethaboxam: a new Oomycetes fungicide," BCPC Conference—Pests & Diseases, vol. 1, 2002, pp. 377-382 (1 page abstract only provided).
U.S. Office Action for U.S. Appl. No. 15/746,551, dated Jan. 8, 2019.
U.S. Office Action for U.S. Appl. No. 15/747,628, dated Jul. 11, 2019.

* cited by examiner

PLANT DISEASE CONTROL COMPOSITION AND PLANT DISEASE CONTROL METHOD

TECHNICAL FIELD

The present invention relates to a composition for controlling plant diseases and a method for controlling plant diseases.

BACKGROUND ART

New strain of *Bacillus*, APM-1 (deposited under ATCC Accession No. PTA-4838), has been known as an active ingredient of compositions for controlling plant diseases and disclosed, for example, in Patent Document 1. Also, ubiquinol oxidase Qo site inhibitors were known as an active ingredient of compositions for controlling plant diseases and disclosed, for example, in Non-Patent Document 1. There is need for a material which is still more effective for controlling plant diseases.

PRIOR ART DOCUMENTS

Patent Documents

Patent Document 1: WO 2003/055303

Non-Patent Document

Non-Patent Document 1: The Pesticide Manual-16th edition (BCPC, ISBN: 978-1-901396-86-7)

DISCLOSURE OF THE INVENTION

Problems to be Solved by the Invention

Damage from plant disease is a cause of considerable loss of crop production, and there is a need to control such plant disease more effectively. Thus, it is an object of the present invention to provide a composition having an excellent controlling effect against plant diseases.

Means for Solving the Problems

The present inventors intensively studied to achieve the above object and have found that a composition comprising *Bacillus* strain APM-1 which has been deposited under ATCC Accession No. PTA-4838 (New strain of *Bacillus*, APM-1) and one or more ubiquinol oxidase Qo site inhibitor has an excellent controlling effect against plant diseases.

Thus, the present invention includes the following [1] to [8].

[1] A composition for control plant diseases comprising *Bacillus* strain APM-1 (New strain of *Bacillus*, APM-1) deposited under ATCC Accession No. PTA-4838 and one or more ubiquinol oxidase Qo site inhibitor.

[2] The composition according to [1] wherein the ubiquinol oxidase Qo site inhibitor is selected from the group consisting of azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin.

[3] The composition according to [1] or [2] comprising the ubiquinol oxidase Qo site inhibitor in an amount of $10^{-10}$ to $1.5 \times 10^7$ g per $10^{10}$ cfu of *Bacillus* strain APM-1.

[4] A plant seed or a vegetative propagation organ comprising *Bacillus* strain APM-1 (New strain of *Bacillus*, APM-1) deposited under ATCC Accession No. PTA-4838 and one or more ubiquinol oxidase Qo site inhibitor.

[5] The plant seed or a vegetative propagation organ according to [4] wherein the ubiquinol oxidase Qo site inhibitor is selected from the group consisting of azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin.

[6] The plant seed or vegetative propagation organ according to [4] or [5] comprising $10^4$ to $10^{14}$ cfu of *Bacillus* strain APM-1 and 0.000001 to 15 g of the ubiquinol oxidase Qo site inhibitor, per 1 kg of the seed or vegetative propagation organ.

[7] A method for controlling plant diseases, comprising a step of applying *Bacillus* strain APM-1 (New strain of *Bacillus*, APM-1) deposited under ATCC Accession No. PTA-4838 and one or more ubiquinol oxidase Qo site inhibitor to a plant or a plant cultivation site.

[8] The method for controlling plant diseases according to [7] wherein the plant is a genetically modified plant.

Effect of Invention

The present invention provides an excellent composition for protecting seeds or vegetative propagation organs and plants grown therefrom from plant diseases.

DESCRIPTION OF EMBODIMENTS

The composition for controlling plant diseases of the present invention (hereinafter referred to as "the present composition") contains *Bacillus* strain APM-1 (New strain of *Bacillus*, APM-1) deposited under ATCC Accession No. PTA-4838 (hereinafter referred to as "the present bacterial strain") and one or more ubiquinol oxidase Qo site inhibitor compound (hereinafter referred to as "the present compound").

The present bacterial strain has been disclosed in WO 2003/055303 and deposited under the name "New strain of *Bacillus*, APM-1" under ATCC Accession No. PTA-4838 at ATCC (American Type Culture Collection). WO 2003/055303 describes that the strain is most similar to *Bacillus amyloliquefaciens*. The present bacterial strain is available from ATCC and can be cultured by a known procedure. The culture may be used as it is or may be separated and concentrated using a conventional industrial technique, such as, not limited to, membrane separation, centrifugal separation, or filtration separation. The fraction of the present bacterial strain thus obtained may be used directly as it contains certain water in the present composition, or if necessary, a dried product obtained by a dry method, such as freeze-dry or spray drying, may be used as the present bacterial strain.

In the present composition for controlling plant diseases, the present compound to be used in combination with the present bacterial strain is not limited, so long as it has an inhibitory effect on ubiquinol oxidase Qo site, but includes, for example, azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin, and preferably, azoxystrobin, pyraclostrobin, picoxystrobin, trifloxystrobin, mandestrobin, and fluoxastrobin.

Azoxystrobin is a known compound and has been described, e.g., on page 63 in "The Pesticide Manual-16th edition (Published by BCPC): ISBN 978-1-901396-36-7".

Azoxystrobin can be obtained from a commercially available formulation or produced by a known method.

Pyraclostrobin is a known compound and has been described, e.g., on page 963 in "The Pesticide Manual-16th edition (Published by BCPC): ISBN 978-1-901396-36-7". Pyraclostrobin can be obtained from a commercially available formulation or produced by a known method.

Picoxystrobin is a known compound and has been described, e.g., on page 901 in "The Pesticide Manual-16th edition (Published by BCPC): ISBN 978-1-901396-36-7". Picoxystrobin can be obtained from a commercially available formulation or produced by a known method.

Trifloxystrobin is a known compound and has been described, e.g., on page 1157 in "The Pesticide Manual-16th edition (Published by BCPC): ISBN 978-1-901396-36-7". Trifloxystrobin can be obtained from a commercially available formulation or produced by a known method.

Mandestrobin is a known compound. Mandestrobin can be obtained from a commercially available formulation or produced by a known method.

Fluoxastrobin is a known compound and has been described, e.g., on page 532 in "The Pesticide Manual-16th edition (Published by BCPC): ISBN 978-1-901396-36-7". Fluoxastrobin can be obtained from a commercially available formulation or produced by a known method.

Kresoxim-methyl is a known compound and has been described, e.g., on page 684 in "The Pesticide Manual-16th edition (Published by BCPC): ISBN 978-1-901396-36-7". Kresoxim-methyl can be obtained from a commercially available formulation or produced by a known method.

Metominostrobin is a known compound and has been described, e.g., on page 775 in "The Pesticide Manual-16th edition (Published by BCPC): ISBN 978-1-901396-36-7". Metominostrobin can be obtained from a commercially available formulation or produced by a known method.

Orysastrobin is a known compound and has been described, e.g., on page 830 in "The Pesticide Manual-16th edition (Published by BCPC): ISBN 978-1-901396-36-7". Orysastrobin can be obtained from a commercially available formulation or produced by a known method.

Famoxadone is a known compound and has been described, e.g., on page 449 in "The Pesticide Manual-16th edition (Published by BCPC): ISBN 978-1-901396-36-7". Famoxadone can be obtained from a commercially available formulation or produced by a known method.

Fenamidon is a known compound and has been described, e.g., on page 452 in "The Pesticide Manual-16th edition (Published by BCPC): ISBN 978-1-901396-36-7". Fenamidon can be obtained from a commercially available formulation or produced by a known method.

Pyribencarb is a known compound and has been described, e.g., on page 977 in "The Pesticide Manual-16th edition (Published by BCPC): ISBN 978-1-901396-36-7". Pyribencarb can be obtained from a commercially available formulation or produced by a known method.

The present composition can be prepared typically by mixing the present bacterial strain and the present compound, respectively, with a solid carrier or a liquid carrier, with addition of a surfactant or other auxiliary agents for formulation if necessary, followed by combining the present bacterial strain formulation and the compound formulation thus obtained. Alternatively, the present composition can be prepared by mixing the present bacterial strain with the present compound in advance, adding a solid carrier or a liquid carrier, with addition of a surfactant or other auxiliary agents for formulation if necessary, followed by formulating into a single formulation.

Examples of the solid carrier include mineral fine powders, such as kaolin clay, pyrophyllite clay, bentonite, montmorillonite, diatomaceous earth, synthetic hydrous silicon oxide, acidic clay, talc, clay, ceramic, quartz, sericite, vermiculite, pearlite, Oya stone, anthracite, limestone, coalite, and zeolite, inorganic compounds, such as sodium chloride, carbonate, sulfate, nitrate, and urea, organic fine powders, such as rice hulls, bran, wheat flour, and peat moss. Examples of the liquid carrier include water, vegetable oil, animal oil, and mineral oil. Examples of the auxiliary substance for formulation include anti-freezing agents, such as ethylene glycol, and propylene glycol, and thickening agents, such as carboxymethyl cellulose, and xanthan gum.

The present composition may contain the present bacterial strain in an effective amount, for example, at least $10^4$ cfu, typically $10^4$ to $10^{13}$ cfu, and preferably $10^7$ to $10^{12}$ cfu of the bacteria per 1 g of the present composition.

The present composition may contain the present compound in an effective amount, for example, typically 0.0001 to 0.90 g, preferably 0.001 to 0.80 g, per 1 g of the present composition.

The present composition typically contains $10^{-10}$ to $1.5 \times 10^7$ g, preferably $10^{-7}$ to $10^5$ g, more preferably $10^{-5}$ to $10^2$ g of the present compound per $10^{10}$ cfu of the present bacterial strain.

The term "effective amount" as used herein refers to an amount of the present bacterial strain and the present compound that is able to exert the controlling effect against plant diseases.

The method of the invention for controlling plant diseases (hereinafter referred to as "the present controlling method") comprises a step of applying the present bacterial strain and one or more of the present compounds to a plant or a plant cultivation site.

In the present controlling method, the present bacterial strain and the present compound to be used are typically those which have been formulated and may be applied as separate formulations or as a present composition. The separate formulations may be applied simultaneously or independently.

In the present controlling method, the present bacterial strain and the present compound are applied in an effective amount.

In the present invention, examples of the cultivation site of the plant include paddy field, cultivated field, tea field, fruit orchard, non-agricultural land, seedling tray and nursery box, nursery soil and nursery mat, water culture medium in hydroponic farm, and the like. The plant disease may have already or not yet occurred in a cultivation site of plant or a place of disease occurrence.

In the present controlling method, examples of the method for treating the present bacterial strain and the present compound include foliage treatment, soil treatment, root treatment, seed treatment and vegetative propagation organ treatment.

Examples of the foliage treatment include treatment of the surface of the cultivated plant with spraying onto the foliage and stem.

Examples of the root treatment include immersing whole plant or a root of the plant in a solution containing the present bacterial strain and the present compound, as well as attaching a solid preparation containing the present bacterial strain, the present compound and a solid carrier to a root of the plant.

Examples of the soil treatment include soil broadcast, soil incorporation and chemical irrigation to soil.

Examples of the seed treatment and vegetative propagation organ treatment include applying seed treatment or vegetative propagation treatment using the present composition, specifically, such as spray treatment wherein a suspension of the present composition is sprayed onto the surface of the seed or the vegetative propagation organ, wet powder coating treatment wherein the present composition in a form of wettable powder is coated onto moist seed or vegetative propagation organ, smearing treatment wherein a liquid of the present composition prepared from wettable powder, emulsifiable concentrate or flowable formulation of the present composition, with addition of water if necessary, is applied onto seed or vegetative propagation organ, immersion treatment wherein seeds or vegetative propagation organs are immersed in a liquid containing the present composition for a certain period of time, and film coating treatment and pellet coating treatment of seeds with the present composition.

In the present invention, the simply described "plant" encompasses in its meaning "a seed of the plant" and "a vegetative propagation organ of the plant".

The term "vegetative propagation organ" as used herein means a part of root, stem, leaf or the like of the plant having the ability to grow when it is separated from the body and placed on soil, such as flower bulb, potato tuberous root, stem tuber, scaly bulb, corm, rhizophore, and strawberry runner.

In the present controlling method, the amount of the present bacterial strain and the present compound in the treatment varies depending on the kind of plant to be treated, the kind of plant disease to be targeted, and the occurrence frequency, the formulation form, the treatment period, the treatment method, the place to be treated, the weather condition or the like, and when a stem and a leaf of the plant or a soil where the plant grows is treated, the amount of the present bacterial strain for the treatment is usually $10^5$ to $10^{19}$ cfu, preferably $10^7$ to $10^{17}$ cfu, per 1 ha, and the amount of the present compound for the treatment is usually 10 to 5000 g, preferably 20 to 2000 g, per 1 ha. The composition in a form of wettable powder, water dispersible granules or the like may be used by diluting with water so that the concentration of the present bacterial strain is usually $10^3$ to $10^{12}$ cfu/L and that the concentration of the present compound is usually 0.0005 to 1% by weight. The composition in a form of dustable powder or granules may be used as it is.

In the seed treatment or vegetative propagation organ treatment, the amount of the present bacterial strain is usually $10^4$ to $10^{14}$ cfu, preferably $10^6$ to $10^{13}$ cfu per 1 kg of the seed or vegetative propagation organ, and the amount of the present compound is usually 0.000001 to 15 g, preferably 0.0001 to 10 g, per 1 kg of the of seed or vegetative propagation organ.

The weight of the seed or vegetative propagation organ means the weight thereof when treating with the present bacterial strain and the present compound or other agricultural chemicals before seeding or burying of the same.

By treating the seed or vegetative propagation organ as described above, a seed or vegetative propagation organ comprising the present bacterial strain and one or more compounds of the invention can be obtained. An adjuvant may be admixed if necessary during the seed treatment or vegetative propagation organs treatment.

Examples of the plant to which the present invention is applicable include the followings.

Agricultural crops: cereal crops, such as corn, wheat, barley, rye, oat, sorghum; pseudocereals, such as buckwheat; pulses, such as soybean, peanut; cotton; sugar beet; rice; oilseed rape; sunflower; sugar cane; tobacco; hop.

Vegetables: solanaceous crops (eggplant, tomato, potato, chili pepper, green pepper, etc.), cucurbitaceae crops (cucumber, pumpkin, zucchini, watermelon, melon, orienta melon, etc.), cruciferous vegetables (radish, turnip, horseradish, kohlrabi, chinese cabbage, cabbage, mustard, broccoli, cauliflower, etc.), asteraceae vegetables (burdock, garland *chrysanthemum*, artichoke, lettuce, etc.), liliaceae vegetables (green onion, onion, garlic, asparagus, etc.), umbelliferae vegetables (carrot, parsley, celery, parsnip, etc.), chenopodiaceae vegetables (spinach, chard, etc.), labiatae vegetables (*perilla*, mint, basil, etc.), leguminous crops (pea, kidney bean, adzuki bean, broad bean, chickpea, etc.), strawberry, sweet potato, yam, taro, konjac, ginger, okra.

Fruit trees: pome fruits (apple, Japanese pear, common pear, Chinese quince, quince, etc.), stone fruits (peach, plum, nectarine, Japanese plum, cherry, apricot, prune, etc.), citrus fruits (Satsuma mandarin, orange, lemon, lime, grapefruit, etc.), nuts (chestnut, walnut, hazel nut, almond, pistachio, cashew nut, macadamia nut, etc.), berries (blueberry, cranberry, blackberry, raspberry, etc.), grape, Japanese persimmon, olive, loquat, banana, coffee, date palm, coconut palm, oil palm.

Trees other than fruit trees: tea, mulberry, flowering trees (azalea, *camellia, hydrangea*, sasanqua, Japanese star anise, cherry, tulip tree, crape myrtle, orange osmanthus, etc.), street trees (ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, yew, elm, horse chestnut, etc.), coral tree, podocarpus, cedar, Japanese cypress, croton, Japanese spindle tree, Japanese *photinia*.

Grasses: *zoysia* (zoysiagrass, *Zoysia matrella*, etc.), bermuda grasses (*Cynodon dactylon*, etc.), bent grasses (*Agrostis alba*, creeping bent grass, hiland bent, etc.), blueglasses (meadow grass, bird grass, etc.), fescue (tall fescue, chewings fescue, creeping red fescue, etc.), ryegrasses (darnel, rye grass, etc.), orchard grass, timothy grass.

Others: flowers (rose, carnation, *chrysanthemum*, prairie gentian, *gypsophila, gerbera*, marigold, *salvia, petunia, verbena*, tulip, aster, gentian, lily, pansy, cyclamen, orchid, *convallaria*, lavender, stock, ornamental cabbage, *primula*, poinsettia, *gladiolus*, cattleya, daisy, cymbidium, *begonia*, etc.), bio-fuel plants (Jatropha, safflower, camelina, switchgrass, *Miscanthus*, reed canary grass, giant reed, kenaf, cassava, willow, etc.), ornamental plants.

The present invention is preferably applied to cereal crops or millets. The present invention is more preferably applied to corn, wheat, sorghum, and soybean.

In the present invention, the variety of plant is not limited so long as it is commonly cultivated. The plants of such varieties include plants which have been conferred with one or more useful trait by a classical breeding technique or a genetic engineering technique (genetically modified plant) as well as stack varieties obtained by crossing such genetically modified plants.

Such useful characters include tolerance to herbicide, plant disease resistance, disease resistance, stress tolerance, and improved quality of crops such as modified fatty acid residue composition of oils and fats.

Examples of the genetically modified plant include those listed in the genetically modified crop registration database (GM APPROVAL DATABASE) in the electronic information site (http://www.isaaa.org/) of the INTERNATIONAL SERVICE for the ACQUISITION of AGRI-BIOTECH APPLICATIONS (ISAAA). More specifically, the plant may be a plant which has been conferred with an environmental stress tolerance, a disease resistance, a herbicide tolerance, a pest resistance or the like, or a plant wherein its trait has been modified with respect to growth and yield, quality of product, sterility or the like, by genetic recombination technology.

Examples of the plant conferred with a herbicide tolerance by gene recombination technology include genetically modified plants conferred with a tolerance to protoporphyrinogen oxidase (herein after referred to as PPO) herbicides such as flumioxazin; 4-hydroxyphenyl pyruvic acid dioxygenase (hereinafter abbreviated as HPPD) inhibitors such as isoxaflutole, mesotrione; acetolactate synthase (hereinafter referred to as ALS) inhibitors such as imazethapyr, thifensulfuron methyl; 5-enolpyruvylshikimate-3-phosphate synthase (hereinafter referred to as EPSP) inhibitors such as glyphosate; glutamine synthetase inhibitors such as glufosinate; auxin herbicides such as 2,4-D, dicamba; and herbicides such as bromoxynil.

Examples of the plant conferred with a herbicide tolerance by gene recombination technology include glyhosate-tolerant genetically modified plants which have been introduced with one or more gene selected from glyphosate tolerant EPSPS gene (CP4 epsps) from *Agrobacterium tumefaciens* strain CP4; glyphosate metabolizing enzyme gene (gat4601, gat6421) which is a gene of glyphosate metabolizing enzyme (glyphosate N-acetyl transferase) from *Bacillus* (*Bacillus licheniformis*) modified by gene shuffling to enhance the metabolic activity; glyphosate metabolizing enzyme (glyphosate oxidase gene, goxv247) from Ochrobactrum (*Ochrobactrum anthropi* strain LBAA), or EPSPS gene having glyphosate-tolerant mutation (mepsps, 2mepsps) from corn. There are glyphosate-tolerant genetically modified varieties with respect to plants such as corn (*Zea mays* L.), soybean (*Glycine max* L.), cotton (*Gossypium hirsutum* L.), sugar beet (*Beta vulgaris*), canola (*Brassica napes, Brassica rapa*), alfalfa (*Medicago sativa*), potato (*Solanum tuberrosum* L), wheat (*Triticum aestivum*), and creeping bent grass (*Agrostis stolonifera*).

Some glyphosate-tolerant genetically modified plants are commercially available. For example, a genetically modified plant expressing glyphosate-tolerant EPSPS from *Agrobacterium* has been marketed under the trade name such as Roundup Ready®, a genetically modified plant expressing glyphosate metabolizing enzyme from *Bacillus* with enhanced metabolic activity by gene shuffling has been marketed under the trade name such as Optimum® GAT®, Optimum® Gly canola, and a genetically modified plant expressing EPSPS gene having glyphosate-tolerant mutation has been marketed under the trade name GlyTol®.

Examples of plants conferred with herbicide-tolerance by gene recombination technology include glufosinate-tolerant genetically modified plants which have been introduced with phosphinothricin N-acetyltransferase (PAT) gene (bar) of the glufosinate metabolizing enzyme from *Streptomyces* (*Streptomyces hygroscopicus*), phosphinothricin N-acetyltransferase gene (pat) of the glufosinate metabolizing enzyme from *Streptomyces* (*Streptomyces viridochromogenes*), a synthesized pat gene, or the like. There are glufosinate-tolerant genetically modified varieties with respect to plants such as corn, soybean, cotton, canola, rice (*Oryza sativa* L.), sugar beet, and cichory (*Cichori intybus*).

Some glufosinate-tolerant genetically modified plants are commercially available. A genetically modified plant expressing glufosinate metabolizing enzyme (bar, pat) from *Streptomyces* has been marked under a trade name including LibertyLink®.

Examples of herbicide-tolerant genetically modified plants include genetically modified plants which have been introduced with the gene (bxn) of nitrilase, which is a bromoxynil-metabolizing enzyme from *Klebsiella* (*Klebsiella pneumoniae* subsp. *Ozaenae*). Bromoxynil-tolerant genetically modified varieties have been produced for plants such as canola, cotton, tobacco (*Nicotiana tabacum* L.) and have been marked under a trade name including Navigator® canola, or BXN®.

Examples of herbicide-tolerant genetically modified plants include genetically modified carnation (*Dianthus caryophyllus*) which has been introduced with ALS herbicide-tolerant ALS gene (SurB, S4-HrA) from tobacco as a selectable marker. Also, a genetically modified larvae (*Linum usitatissumum* L.) which has been introduced with ALS herbicide-tolerant ALS gene from *Arabidopsis* (*Arabidopsis thaliana*) has been developed under the trade name CDC Triffid Flax. Also, a genetically modified soybean which has been introduced with ALS herbicide-tolerant ALS gene (csr1-2) from *Arabidopsis* has been developed under the trade name Cultivance®. Furthermore, there are sulfonylurea/imidazolinone herbicide-tolerant genetically modified corn which has been introduced with ALS herbicide-tolerant ALS gene (zm-hra) from corn, and sulfonylurea herbicide-tolerant genetically modified soybean which has been introduced with ALS herbicide-tolerant ALS gene (gm-hra) from soybean.

Examples of plants conferred with herbicide-tolerance by gene recombination technology include isoxaflutole-tolerant genetically modified soybean which has been introduced with HPPD herbicide-tolerant HPPD gene (hppdPFW 336) from *Pseudomonas* (*Pseudomonas fluorescens* strain A32) and mesotrione-tolerant genetically modified soybean which has been introduced with HPPD gene (avhppd-03) from oats (*Avena sativa*).

Examples of plants conferred with herbicide-tolerance by gene recombination technology include 2,4-D-tolerant genetically modified corns, genetically modified soybeans, genetically modified cottons which have been introduced with gene (aad-1) of 2,4-D metabolizing enzyme aryloxyalkanoate dioxygenase from *Sphingobium* (*Sphingobium herbicidovorans*) or with gene (aad-12) of 2,4-D metabolizing enzyme aryloxyalkanoate dioxygenase from *Delftia* (*Delftia acidovorans*). Some of them are developed under the trade names such as Enlist® Maize, Enlist® Soybean. Also, there are dicamba-tolerant genetically modified soybeans and cottons which have been introduced with gene (dmo) of dicamba monooxygenase, which is dicamba metabolizing enzyme from *Stenotrophomonas* (*Stenotrophomonas maltophilia* strain DI-6).

Examples of genetically modified plant tolerant to two or more herbicides include genetically modified cotton and genetically modified corn, which are tolerant to both glyphosate and glufosinate, and marketed under the trade name such as GlyTol® LibertyLink®, Roundup Ready® LibertyLink® Maize. Also, there are a genetically modified soybean tolerant to both glufosinate and 2,4-D and developed under the trade name Enlist® Soybean, and a genetically modified cotton tolerant to both glufosinate and 2,4-D. A genetically modified soybean tolerant to both glyphosate and dicamba has been developed under the trade name Genuity®) Roundup Ready® 2 Xtend®. Genetically modified corn and soybean resistant to both glyphosate and ALS inhibitors have been developed under the trade name Optimum® GAT®. In addition, a genetically modified cotton tolerant to both glufosinate and dicamba, a genetically modified corn tolerant to both glyphosate and 2,4-D, a genetically modified soybean tolerant to both glyphosate and HPPD herbicide have also been developed. Furthermore, a genetically modified soybean tolerant to three herbicides glyphosate, glufosinate and 2,4-D has been developed.

Examples of the plant conferred with a pest resistance by gene recombination technology include plants conferred with resistance to lepidopteran insects, coccinella insects, multipter insects, nematodes and the like.

Examples of the plant conferred with a pest resistance to lepidopteran insects by genetic recombination technology include genetically modified plants such as soybean, cotton, rice, poplar (*Populus* sp.), and tomato (*Lycopersicon esculentum*), and eggplant (*Solanum melongena*), which have been introduced with a gene encoding delta-endotoxin, which is an insecticidal protein derived from a soil bacterium *Bacillus thuringiensis* bacteria (hereinafter referred to as Bt bacteria). Examples of the delta-endotoxin that confers a pest resistance to lepidopteran insects include Cry1A, Cry1Ab, modified Cry1Ab (truncated Cry1Ab), Cry1Ac, Cry1Ab-Ac (hybrid protein of Cry1Ab and Cry1Ac), Cry1C, Cry1F, Cry1Fa2 (modified cry1F), moCry1F (modified Cry1F), Cry1A. 105 (hybrid protein of Cry1Ab, Cry1Ac and Cry1F), Cry2Ab2, Cry2Ae, Cry9C, Vip3A, Vip3Aa20, and the like.

Examples of the plant conferred with a pest resistance to coccinella insects by genetic recombination technology include genetically modified plants such as corn, potato, which have been introduced with a gene encoding delta-endotoxin, which is an insecticidal protein derived from a soil bacterium Bt bacteria. Examples of the delta-endotoxin that confers a pest resistance to coccinella insects include Cry3A, mCry3A (modified Cry3A), Cry3Bb1, Cry34Ab1, and Cry35Ab1.

Examples of the plant conferred with a pest resistance to multipter insects by genetic recombination technology include genetically modified corn, which has been introduced with a synthetic gene encoding a hybrid protein eCry3.1Ab, which is a hybrid protein of Cry3A and Cry1Ab derived from soil bacteria Bt bacteria, a genetically modified cotton, which has been introduced with a gene encoding trypsin inhibitor CpTI from black-eyed pea (*Vigna unguiculata*), a genetically modified poplar, which has been introduced with a gene encoding API, which is a protease inhibitor protein A from arrowhead (*Sagittaria sagittifolia*).

Examples of the insecticidal protein that confers a pest resistance to the plants include hybrid proteins, truncated proteins, and modified proteins of the insecticidal proteins described above. The hybrid proteins are produced by combining different domains of multiple insecticidal proteins using a common recombination technology, and Cry1Ab-Ac and Cry1A.105 are known.

Examples of the truncated proteins include Cry1Ab lacking the amino acid sequence partially. Examples of the modified proteins include proteins in which one or more amino acids of natural delta-endotoxin have been substituted, such as Cry1Fa2, moCry1F, mCry3A.

Examples of other insecticidal proteins that confer insect resistance to plants by genetic recombination technology include insecticidal proteins from *Bacillus cereus* or *Bacillus popilliae*, the insecticidal proteins Vip 1, Vip 2, Vip 3 of Bt bacteria, insecticidal proteins from nematode, toxin produced by an animal such as scorpotoxin, spider toxin, bee venom or insect-specific neurotoxin, toxins of filamentous fungi, plant lectin, agglutinin, protease inhibitor such as trypsin inhibitor, serine protease inhibitor, patatin, cystatin, papain inhibitor, ribosome inactivating protein (RIP) such as ricin, corn-RIP, abrin, rufin, saporin, bryodin, steroid metabolizing enzymes such as 3-hydroxysteroid oxidase, ecdysteroid-UDP-glucosyltransferase, cholesterol oxidase, ecdysone inhibitor, HMG-CoA reductase, ion channel inhibitors such as sodium channel inhibitor, calcium channel inhibitor, juvenile hormone esterase, diuretic hormone receptor, stilbene synthase, bibenzyl synthase, chitinase, glucanase, and the like.

Genetically modified plants conferred with a pest resistance by introducing one or more insecticidal protein gene are known, and some of such genetically modified plants are commercially available.

Examples of commercially available genetically modified cotton conferred with a pest resistance include Bollgard® cotton expressing the insecticidal protein Cry1Ac of Bt bacteria, Bollgard II® cotton expressing the insecticidal proteins Cry1Ac and Cry2Ab of Bt bacteria, Bollgard III® expressing the insecticidal proteins Cry1Ac, Cry2Ab, Vip3A of Bt bacteria, VIPCOT® expressing the insecticidal proteins Vip3A and Cry1Ac of Bt bacteria, WideStrike® expressing the insecticidal proteins Cry1Ac, Cry1F of Bt bacterium.

Examples of commercially available genetically modified corn conferred with a pest resistance include YieldGard® Rootworm RW expressing the insecticidal protein Cry3Bb1 of Bt bacteria, YieldGard Plus® expressing the insecticidal proteins Cry1Ab and Cry3Bb1 of Bt bacteria, YieldGard® VT Pro® expressing the insecticidal proteins Cry1A.105 and Cry2Ab2 of Bt bacteria. Agrisure® RW expressing the insecticidal protein mCry3A of Bt bacteria, Agrisure® Viptera expressing the insecticidal protein Vip3Aa20 of Bt bacteria, Agrisure® Duracade® expressing the insecticidal protein eCry3.1Ab of Bt bacteria are also commercially available.

Examples of commercially available genetically modified potato conferred with a pest resistance include Atlantic NewLeaf® potato, NewLeaf® Russet Burbank potato, and the like, which express the insecticidal protein Cry3A of Bt bacteria.

Examples of genetically modified plants conferred with resistance to plant diseases include kidney bean (*Phaseolus vulgaris*), papaya (*Carica papaya*), plum (*Prunus domestica*), potato, squash (*Cucurbita pepo*), sweet pepper (*Capsicum annuum*), tomato, and the like, which have been conferred with a resistance to plant viral diseases. Specific examples of genetically modified plants conferred with a resistance to plant viral diseases include a genetically modified kidney bean which has been introduced with a gene that produces double-stranded RNA of a replication protein of bean golden mosaic virus, a genetically modified *papaya* which has been introduced with a coat protein gene of *papaya* ringspot virus, a genetically modified potato which has been introduced with a coat protein gene of potato virus Y or replication enzyme domain gene of potato leaf roll virus, a genetically modified squash which has been introduced with a coat protein gene of Cucumber mosaic virus, with a coat protein gene of Watermelon mosaic virus, or with a coat protein gene of Zucchini yellow mosaic virus, a genetically modified sweet pepper and transgenic tomato which has been introduced with a coat protein gene of Cucumber mosaic virus, and the like.

A genetically modified potato conferred with a resistance to plant viral diseases is commercially available under a trade name including NewLeaf®.

Examples of the plant conferred with a resistance to plant disease also include plants that have been conferred with an ability to produce a selective anti-pathogenic substance using genetic recombination technology. PR proteins are known as an anti-pathogenic substance (PRPs, EP392225). Such anti-pathogenic substance and genetically modified plants that produce the same are described in EP 392225, WO 199533818, EP 353191 and the like. Examples of the anti-pathogenic substance include ion channel inhibitors such as sodium channel inhibitors, calcium channel inhibitors (KP1, KP4, KP6 toxin produced by viruses are known), anti-pathogenic substances produced by microorganisms such as stilbene synthase, bibenzyl synthase, chitinase, glucanase, peptide antibiotics, antibiotics having heterocycles, protein factors involved in plant disease resistance, which is referred to as plant disease resistance genes and described in WO 2003000906.

Examples of genetically modified plant wherein the quality of product has been modified includes genetically modified plants having a modification in lignin production, a modification in oils or fatty acid components, production of phytic acid degrading enzymes, a modification in flower color, a modification in alpha-amylase activity, a modification in amino acids, a modification in starch or carbohydrate components, inhibition of acrylamide production, reduction of black spots due to mechanical damage, anti-allergy, reduction of nicotine production, or retardation of aging or grain-filling.

There is a genetically modified alfalfa wherein the lignin content has been lowered by RNA interference with a gene that generates double-stranded RNA of S-adenosyl-L-methionine: trans-caffeoyl CoA 3-methyltransferase (ccomt) gene of alfalfa related to lignin production.

A genetically modified canola wherein the triacylglyceride content, including lauric acid, has been increased by introducing a gene involved in fatty acid synthesis, 12:0 ACP thioesterase gene of laurier (*Umbellularia californica*), has been developed under the trade name Laurical® Canola.

A genetically modified canola wherein the degradation of endogenous phytic acid has been enhanced by introducing a gene (phyA) of 3-phytase, which is a degrading enzyme of phytic acid of plants from *Aspergillus niger*, has been developed under the trade name Phytaseed® Canola. Also, a genetically modified corn wherein the degradation of endogenous phytic acid has been enhanced by introducing 3-phytase gene (phyA) of *Aspergillus niger* has been developed.

A genetically modified carnation wherein the flower color has been controlled to blue by introducing a gene of dihydroflavonol-4-reductase, which is an enzyme that produces blue pigment delphinidin and its derivative of *petunia* (*Petunia hybrida*), and a flavonoid-3',5'-hydroxylase gene from *petunia*, pansy (*Viola wittrockiana*), salvia (*Salvia splendens*) or carnation is known. Genetically modified carnations with flower color controlled to blue have been developed under the trade name such as Moonldust®, Moonshadow®, Moonshade®, Moonlite®, Moonaqua®, Moonvista®, Moonique®, Moonpearl®, Moonberry Registered trademark), and Moonvelvet®. Also, genetically modified roses with flower color controlled to blue by introducing a gene of anthocyanin-5-acyltransferase, which is an enzyme that produces blue pigment delphinidin and its derivative, from Torenia (*Torenia* sp.), and a flavonoid-3', 5'-hydroxylase gene from pansy have been developed.

A genetically modified corn wherein the production of bioethanol has been increased by introducing a gene (Amy797E) of heat-resistant alpha-amylase relating to starch degradation of *Thermococcales* sp. have been developed under the trade name Enogen®.

A genetically modified corn wherein the production of lysine has been increased by introducing a gene (cordapA) of dihydrodipicolinate synthase relating to the production of amino acid lysine of *Corynebacterium glutamicum* has been developed under the trade name including Mavera®.

A genetically modified melon and a genetically modified tomato wherein the shelf life has been improved by introducing a gene (sam-K) of S-adenosylmethionine hydrolase relating to ethylene production by plant hormones from *Escherichia coli* bacteriophage T3 has been developed. Also, genetically modified tomatoes with improved shelf life by introducing a gene that lacks a part of the ACC synthase gene, which is involved in the ethylene production by plant hormones, from tomato, an ACC deaminase gene from *Pseudomonas* (*Pseudomonas chlororaphis*) that degrades the ethylene precursor ACC, a gene that generates double-stranded RNA of polygalacturonase genes which degrades cell wall pectin, or ACC oxidase genes of tomato related to the production of ethylene have been developed. A genetically modified tomato with improved shelf life by introducing a gene that produces double-stranded RNA of polygalacturonase genes of tomato has been developed under the trade name FLAVR SAVR®.

A genetically modified potato, wherein the possibility of decomposition of starch, formation of black spots due to mechanical damage and production of a carcinogen (acrylamide) from heating are lowered by introducing a gene that generates double-stranded RNA of a transcription factor promoting degradation of starch derived from potato, and a gene that generates double-stranded RNA of polyphenol oxidase gene and a gene that generates double-stranded RNA of genes involved in asparagine production from potato, has been developed under a trade mark including Innate®. Also, a genetically modified potato wherein the amylose content is lowered by introducing an antisense gene of starch synthase from potato has been developed under the trade name Amflora®.

A genetically modified rice having alleviation effect on pollinosis with immune tolerance by introducing a gene (7crp) of altered antigenic protein of cedar pollen has been developed.

A genetically modified soybean wherein the oleic acid content is increased by introducing a partial gene (gm-fad2-1) of ω-6 desaturase, which is a fatty acid desaturase enzyme, of soybean to inhibit the gene expression thereof has been developed under the trade name Plenish® or Treus®. Also, a genetically modified soybean wherein the saturated fatty acid content is lowered by introducing a gene (fatb1-A) that generates a double-stranded RNA of acyl-acyl carrier protein-thioesterase and a gene (fad2-1A) that generates a double-stranded RNA of δ-12 desaturase has been developed under the trade name Vistive Gold®. Also, a genetically modified soybean wherein the ω3 fatty acid content is enhanced by introducing a δ-6 desaturase gene (Pj.D6D) of primrose and a δ-12 desaturase gene (Nc.Fad3) of *Neurospora crassa* has been developed.

A genetically modified tobacco wherein the nicotine content is lowered by introducing an antisense gene of quinolinic acid phosphoribosyltransferase (NtQPT1) of tobacco has been developed.

A genetically modified rice, Golden rice, introduced with a phytoene synthase gene (psy) of trumpet *narcissus* (*Narcissus pseudonarcissus*) and a carotene desaturase gene (crt1) of soil bacteria that synthesizes carotenoids (*Erwinia uredovora*), which allow endosperm-specific expression to produce β-carotene in endosperm tissue, whereby a rice containing vitamin A is enabled to be harvested, has been developed.

Examples of the plants in which the fertile trait has been modified by a genetic recombination technique include genetically modified plants conferred with male sterility and fertility restoration. There are genetically modified corn and chicory conferred with male sterility by introducing anther tapetum cell expressing a ribonuclease gene (barnase) of *Bacillus* (*Bacillus amyloliquefaciens*). There is also a genetically modified corn conferred with male sterility by introducing a DNA adenine methyltransferase gene (dam) of *Escherichia coli*. Furthermore, there is a genetically modified corn wherein the sterility has been controlled by introducing alpha-amylase gene (zm-aa1) of corn that confers male sterility and ms45 protein gene (ms45) of corn that confers fertility restoration.

There is a genetically modified canola conferred with a fertility restoring function by introducing anther tapetum cells expressing a ribonuclease inhibitory protein gene (barstar) of *Bacillus*. In addition, there is a genetically modified canola wherein the sterility has been controlled by introducing a ribonuclease gene (barnase) of *Bacillus* that confers a male sterility and a ribonuclease inhibitory protein gene (barstar) of *Bacillus* that confers a fertility restoration.

Examples of the plants conferred with tolerance to environmental stress by a genetic recombination technique include genetically modified plants conferred with tolerance to dryness. A dry tolerant corn which has been introduced with a cold shock protein gene (cspB) of *Bacillus subtilis* has been developed under the trade name Genuity® Drought-Gard®. Also, dry tolerant sugar cane which has been introduced with choline dehydrogenase gene (RmBetA) of alfalfa rhizobium (*Rhizobium meliloti*) or *E. coli* (*Esherichia coli*) has been developed.

Examples of the plants wherein a trait related to growth and yield has been modified by genetic recombination technology include genetically modified plants having enhanced growth ability. For example, a genetically modified soybean which has been introduced with a gene of *Arabidopsis* encoding a transcription factor that controls circadian rhythm (bbx32) has been developed.

The plant according to the present invention can be a plant which has been modified using other techniques than genetic recombination technology. More specifically, it may be a plant which has been conferred with tolerance to environmental stress, disease resistance, tolerance to herbicide, insect resistance, or the like, by classical breeding technique, genetic marker breeding technique, genome editing technique, or the like.

Examples of the plant wherein a tolerance to herbicide has been conferred by classical breeding technique or genetic marker breeding technique include corn, rice, wheat, sunflower (*Helianthus annuus*), canola, and lentil beans (*Lens culinaris*), which are resistant to imidazolinone type ALS inhibiting herbicides, such as imazethapyr, and are marketed under the trade name Clearfield®. Also, there is STS soybean, which is a soybean tolerant to sulfonylurea-based herbicide, as an example of plants which has been conferred with a resistance to sulfonyl-based ALS-inhibiting herbicides such as thifensulfuron methyl by genetic marker breeding technique. Also, there is SR corn, which is resistant to sethoxydim, as an example of plants which has been conferred with a resistance to acetyl CoA carboxylase inhibitor, such as trione oxime type herbicide, aryloxyphenoxypropionic acid type herbicide, by genetic marker breeding technique.

Examples of the plants conferred with pest resistance by classic or genetic marker breeding technique include a soybean having Rag 1 (Resistance Aphid Gene 1) gene, which is an aphid resistant gene. Examples of the plants conferred with resistance to nematodes by the classical breeding technique include a soybean conferred with a resistance to Cysto nematode, and a cotton conferred with a resistance to Root Knot nematode.

Examples of the plants which has been conferred with a resistance to plant disease by classic or genetic marker breeding technique include a corn which has been conferred with a resistant to anthracnose stalk rot, a corn which has been conferred with a resistant to Gray leaf spot, a corn which has been conferred with a resistant to Goss's wilt, a corn which has been conferred with a resistant to *Fusarium* stalk rot, a soybean which has been conferred with a resistant to Asian soybean rust, a pepper which has been conferred with a resistant to *Phytophthora*, a lettuce which has been conferred with a resistant to powdery mildew, a tomato which has been conferred with a resistant to Bacterial wilt, a tomato which has been conferred with a resistant to Gemini virus, and a lettuce which has been conferred with a resistant to downy mildew.

As an example of the plants which have been conferred with a tolerance to dryness by classic or genetic marker breeding technique, a dry tolerant corn has been developed under the trade name such as Agrisure Artesian®, Optimum AQUA Max®.

As an example of the plants conferred with a tolerance to herbicide by genomic editing technique, a canola conferred with a tolerance to sulfonylurea herbicide by rapid breed development technology wherein a mutation to confer tolerance to sulfonylurea herbicide has introduced into ALS gene via chimera oligonucleotides of DNA and RNA, has been developed under the trade name SU Canola®.

The above plants include a variety which has been conferred with two or more traits, such as tolerance to environmental stress, disease resistance, tolerance to herbicide, pest resistance, growth and yield traits, quality of product, and sterility, using a genetic recombination technology as described above, such as a classic breeding technique, a genetic marker breeding, or a genome editing technique, as well as a variety which has been conferred with two or more traits from parents by crossing the parents, which are genetically modified plants having same or different characteristic. Examples of such plant include genetically modified plants conferred with both of tolerance to herbicide and pest resistance.

For example, as for a genetically modified plant conferred with tolerance to glyphosate and pest resistance, genetically modified cottons, such as Roundup Ready® Bollgard® cotton, Roundup Ready® Bollgard II® cotton, Roundup Ready® Flex® Bollgard cotton, Bollgard® III x Roundup Ready® Flex®, and VIPCOT® Roundup Ready Flex® Cotton, have been developed. Also, genetically modified soybeans have been developed under the trade name, such as Agrisure® GT/RW, Roundup Ready® YieldGard® maize, Genuity® VT Double Pro®, Genuity® VT Triple Pro®, YieldGard®, YieldGard® CB+RW, YieldGard® VT® Rootworm® RR 2, YieldGard® RW+RR, YieldGard® VT Triple, or YieldGard® Plus with RR. Furthermore, a genetically modified soybean such as Intacta® Roundup Ready® 2 Pro has been developed.

For example, as for genetically modified plants conferred with tolerance to glufosinate and pest resistance, genetically modified cottons have been developed under the trade name, such as Widestrike® Cotton, Twinlink® Cotton, and Fiber- Max® LibertyLink® Bollgard II®. Also, genetically modified corns have been developed under the trade name, such as Agrisure® CB/LL, Agrisure® CB/LL/RW, Agrisure® Viptera® 2100, Agrisure® Viptera® 3100, Bt Xtra Maize, NaturGard Knockout®, Herculex® RW, Herculex® CB, Herculex® XTRA, Starlink® Maize, and Liberty Link® YieldGard® Maize.

For example, as for genetically modified plants conferred with tolerance to glyphosate and glufosinate and pest resistance, genetically modified cottons have been developed under the trade name, such as Widestrike® Roundup Ready® Cotton, Widestrike® Roundup Ready Flex® Cotton, Widestrike® Cotton, Registered trademark) x Roundup Ready Flex® x VIPCOT® Cotton, and Glytol® x Twinlink®. Also, genetically modified corns have been developed under the trade name, such as Agrisure® GT/CB/LL, Agrisure® 3000GT, Agrisure® 3122, Agrisure® Viptera® 3110, Agrisure® Viptera 3111, Agrisure® Viptera® 3220, Agrisure® Duracade® 5122, Agrisure® Duracade® 5222, Optimum® Intrasect, Optimum® TRIsect, Optimum® Intrasect XTRA, Optimum® Intrasect Xtreme, Genuity® martStax®, Power Core®, Herculex® I RR, Herculex® RW Roundup Ready® 2, and Herculex XTRA® RR.

For example, as for genetically modified plants conferred with tolerance to bromoxynil and pest resistance, a genetically modified cottons has been developed under the trade name, such as BXN® Plus Bollgard® Cotton.

Examples of a variety conferred with two or more traits include genetically modified plants conferred with disease resistance and pest resistance. For example, as for genetically modified plants conferred with resistance to potato virus Y and pest resistance, genetically modified potatoes have been developed under the trade name, such as Hi-Lite NewLeaf® Y Potato, NewLeaf® Y Russet Burbank Potato, and Shepody NewLeaf® Y potato. As for genetically modified plants conferred with resistance to potato leaf roll virus and pest resistance, genetically modified potatoes have been developed under the trade name, such as NewLeaf® Plus Russet Burbank Potato.

Examples of a variety conferred with two or more traits include genetically modified plants conferred with tolerance to herbicide and altered product quality. For example, a genetically modified canola and genetically modified corn, which have been conferred with tolerance to glufosinate and fertile trait have been developed under the trade name, such as InVigor® Canola and InVigor® Maize, respectively.

Examples of a variety conferred with two or more traits include genetically modified plants conferred with a pest resistance and altered product quality. For example, a genetically modified corn conferred with resistance to lepidopterous insects and a trait of enhanced lysine production has been developed under the trade name such as Mavera® YieldGard® Maize.

For other Examples of a variety conferred with two or more traits as mentioned above, genetically modified plants conferred with tolerance to herbicide and a trait altering fertility, genetically modified plants conferred with tolerance to herbicide and tolerance to environmental stress, genetically modified plants conferred with tolerance to herbicide and a trait modifying growth and yield, genetically modified plants conferred with tolerance to herbicide, pest resistance, and a trait modifying product quality, genetically modified plants conferred with tolerance to herbicide, pest resistance, and tolerance to environmental stress, have been developed.

Examples of the plant diseases which can be controlled according to the present invention include the followings.

Diseases of rice: blast (*Magnaporthe oryzae*), brown spot (*Cochliobolus miyabeanus*), sheath blight (*Rhizoctonia solani*), "Bakanae" disease (*Gibberella fujikuroi*), seedling blight (*Pythium arrhenomanes, Pythium graminicola, Pythium spinosum, Pythium* sp., *Rhizopus chinensis, Rhizopus oryzae, Trichoderma viride*);

Diseases of wheat: powdery mildew (*Erysiphe graminis*), Fusarium blight (*Fusarium graminearum, F. avenaceum, F. culmorum, F. asiaticum, Microdochium nivale*), rust (*Puccinia striiformis, P. graminis, P. recondita, P. hordei*), snow mold (*Typhula* sp., *Micronectriella nivalis*), loose smut (*Ustilago tritici, U. nuda*), stinking smut (*Tilletia caries*), eye spot (*Pseudocercosporella herpotrichoides*), scald (*Rhynchosporium secalis*), speckled leaf blotch (*Septoria tritici*), glume blotch (*Leptosphaeria nodorum*), net blotch (*Pyrenophora teres Drechsler*), yellow spot (*Pyrenophora tritici-repentis*), stripe (*Pyrenophora graminea*), Rhizoctonia damping-off (*Rhizoctonia solani*), snow mold (*Typhula ishikariensis, Typhula incarnata, Sclerotinia borealis, Microdochium nivale*), foot lot disease (*Fusarium graminearum*);

Diseases of corn: smut (*Ustilago maydis*), brown spot (*Cochliobulus heterostrophus*), zonate leaf spot (*Gloeocercospora sorghi*), southern rust (*Puccinia polysora*), grey leaf spot (*Cercospora zaea-maydis*), Rhizoctonia danpimg-off (*Rhizoctonia solani*), gibberella ear rot (*Fusarium moniliforme*), anthracnose (*Colletotrichum graminicola*), seedling blight (*Fusarium* spp., *Rhizoctonia solani*);

Diseases of citrus: black leaf spot (*Diaporthe citri*), scab (*Elsinoe fawcetti*), fruit rot (*Penicillium digitatum, P. italicum*); brown rot (*Phytophthora parasitica, Phytophthora citrophthora*);

Diseases of apple: Monilia leaf blight (*Monilinia mali*), Valsa canker (*Valsa ceratosperma*), powdery mildew (*Podosphaera leucotricha*), Alternaria blotch (*Alternaria alternate* apple pathotype), scab (*Venturia inaequalis*), anthracnose (*Colletotrichum gloeosporioies, Colletotrichum acutatum*), Phytophthora rot (*Phytophtora cactorum*); blotch (*Diplocarpon mali*); ring rot (*Botryosphaeria berengeriana*);

Diseases of pear: scab (*Venturia nashicola, V. pirina*), black spot (*Alternaria* alternate Japanese. pear pathotype), rust (*Gymnosporangium haraeanum*), Phytophthora fruit rot (*Phytophthora cactorum*);

Diseases of peach: brown rot (*Monilinia fructicola*), scab (*Cladosporium carpophilum*), Phomopsis seed decay (*Phomopsis* sp.);

Diseases of grape: anthracnose (*Elsinoe ampelina*), ripe rot (*Colletorichum gloeosporioides, Colletotrichum acutatum*), powdery mildew (*Uncinula necator*), rust (*Phakopsora ampelopsidis*), black rot (*Guignardia bidwellii*), downy mildew (*Plasmopara viticola*), gray mold (*Botrytis cinerea*);

Diseases of persimmon: anthracnose (*Gloeosporium kaki*), leaf spot (*Cercospora kaki, Rycosphaerella nawae*);

Diseases of cucumbers: anthracnose (*Colletotrichum orbiculare*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora blight (*Phytophthora* sp.), damping-off (*Pythium* sp.); Rhizoctonia damping-off (*Rhizoctonia solani*);

Diseases of tomato: Early blight (*Alternaria solani*), Leaf mold (*Cladosporium fulvum*), late blight (*Phytophthora infestans*), leaf spot (*Stemphylium lycoperici*);

Diseases of eggplant: brown spot (*Phomopsis vexans*), powdery mildew (*Erysiphe cichoracearum*);

Diseases of *brassica* vegetables: *Alternaria* leaf spot (*Alternaria japonica*), leaf spot (*Cercosporella brassicae*), Clubroot (*Plasmodiophora brassicae*), downy mildew (*Peronospora parasitica*), root rot (*Phoma* lingam);

Diseases of rapeseed: *Sclerotinia* rot (*Sclerotinia sclerotiorum*), *Alternaria* leaf spot (*Alternaria brassicae*), powdery mildew (*Erysiphe cichoracearum*), black leg (*Leptosphaeria maculans*), *Rhizoctonia* damping-off (*Rhizoctonia solani*);

Diseases of green onion: rust (*Puccinia allii*), *Fusarium* wilt (*Fusarium oxysoporum*);

Diseases of onion: gray-mold neck rot (*Botrytis allii*), leaf blight (*Botrytis squamosa*), *Fusarium* basal rot (*Fusarium oxysoporum, Fusarium solani*);

Diseases of soybean: purple stain (*Cercospora kikuchii*), anthracnose (*Elsinoe glycines*), pod and stem blight (*Diaporthe phaseolorum* var. *Sojae*), brown spot (*Septoria glycines*), leaf spot (*Cercospora sojina*), fust (*Phakopsora pachyrhizi*), *Fusarium* blight (*Phytophthora sojae*), damping-off (*Rhizoctonia solani*), root necrosis (*Rhizoctonia solani*), *Fusarium* root necrosis (*Fusarium solani*), anthracnose (*Colletotrichum truncatum*), *Fusarium* blight (*Fusarium oxysporum, F. avenaceum, F. roseum*), *Sclerotinia* rot (*Sclerotinia sclerotiorum*);

Diseases of adzuki bean: gray mold (*Botrytis cinerea*), *Sclerotinia* rot (*Sclerotinia sclerotiorum*), rust (*Uromyces phaseoli*), anthracnose (*Coletotrichum phaseolorum*);

Diseases of kidney bean: gray mold (*Botrytis cinerea*), *Sclerotinia* rot (*Sclerotinia sclerotiorum*), anthracnose (*Colletotrichum lindemthianum*), *Fusarium* wilt (*Fusarium oxysporum*), rust (*Uromyces phaseoli*), angular leaf spot (*Phaeoisariopsis griseola*), *Rhizoctonia* root necrosis (*Rhizoctonia solani*), aphanomyces root necrosis (*Aphanomyces euteiches*);

Diseases of peanut: leaf spot (*Cercospora personata*), brown leaf spot (*Cercospora arachidicola*), southern blight (*Sclerotium rolfsii*);

Diseases of pea: powdery mildew (*Erysiphe pisi*), root necrosis (*Fusarium solani* f. Sp. *Pisi*);

Diseases of potato: early blight (*Alternaria solani*), late blight (*Phytophthora infestans*), powdery scab (*Spongospora subterranea*), pink rot (*Phytophthora erythroseptica*);

Diseases of strawberry: powdery mildew (*Sphaerotheca hamuli*), anthracnose (*Glomerella cingulata*);

Diseases of tea: net blister blight (*Exobasidium reticulatum*), white scab (*Elsinoe leucospila*), gray blight (*Pestalotiopsis* sp.), anthracnose (*Colletotrichum* theae-*sinensis*);

Diseases of cotton: *Fusarium* wilt (*Fusarium oxysporum*), *Fusarium* wilt (*Rhizoctonia solani*);

Diseases of tobacco: brown spot (*Alternaria longipes*), powdery mildew (*Erysiphe cichoracearum*), anthracnose (*Colletotrichum tabacum*), downy mildew (*Peronospora tabacina*), black shank (*Phytophthora nicotianae*);

Diseases of sugar beet: brown leaf spot (*Cercospora beticola*), leaf blight (*Thanatephorus cucumeris*), root necrosis (*Thanatephorus cucumeris*), aphanomyces root rot (*Aphanomyces cochlioides*);

Diseases of rose: scab (*Diplocarpon rosae*), powdery mildew (*Sphaerotheca pannosa*), downy mildew (*Peronospora sparsa*);

Diseases of chrysanthemum: brown leaf spot (*Septoria chrysanthemi-indici*), rust (*Septoria chrysanthemi-indici*), downy mildew (*Bremia lactucae*);

Diseases of radish: *alternaria* leaf spot (*Alternaria brassicicola*);

Disease of turfgrass: dollar spot (*Sclerotinia homeocarpa*), brown patch and large patch (*Rhizoctonia solani*);

Diseases of banana: Sigatoka disease (*Mycosphaerella fijiensis, Mycosphaerella musicola, Pseudocercospora musae*);

Diseases of sunflower: downy mildew (*Plasmopara halstedii*), alternaria leaf spot (*Alternaria helianthi*), southern blight (*Sclerotium rolfsii*), damping-off (*Rhizoctonia solani*), *Sclerotinia* rot (*Sclerotinia sclerotiorum*), rust (*Puccinia helianthi*);

Diseases of various plants: diseases caused by *Pythium* spp. (*Pythium aphanidermatum, Pythium debarianum, Pythium graminicola, Pythium irregulare, Pythium ultimum*), gray mold (*Botrytis cinerea*), *Sclerotinia* rot (*Sclerotinia sclerotiorum*); damping-off (*Rhizoctonia solani*).

The present invention can be applied preferably to *Pythium* spp., *Rhizoctonia* spp., *Fusarium* spp., *Phomopsis* spp., and particularly, to *Pythium* spp., *Rhizoctonia* spp.

EXAMPLES

The invention is described in more detail with reference to the following Preparation Examples, Formulation Examples, Seed Treatment Examples, and Test Examples, which are not intended to limit the scope of the present invention. The term "part" means "part by weight" unless otherwise specified.

Preparation Examples are provided below.

Preparation Example 1

A culture broth of the present bacterial strain, which has been cultured by a known technique, is centrifuged according to an ordinary method to separate into a supernatant and a precipitate. The supernatant is removed, and the precipitate is washed with sterilized water to obtain a bacterial mass. The obtained bacterial mass is suspended in water, dried on spray drier, and the resultant dried product is pulverized to obtain a powder of the present bacterial strain.

Preparation Example 2

A culture broth of the present bacterial strain, which has been cultured by a known technique, is frozen at −80° C., freeze-dried and pulverized to obtain a powder of the present bacterial strain.

Preparation Example 3

In a 500 mL Erlenmeyer flask with baffle, a platinum loop scraping of the present bacterial strain, which have been cultured in TSA (an agar medium containing 15 g/L of casein peptone, 5 g/L of soybean peptone, 5 g/L of sodium chloride, and 15 g/L of agar), are inoculated to a liquid medium containing 200 mL TSB (a liquid medium containing 17 g/L of casein peptone, 3 g/L of soybean peptone, 2.5 g/L of glucose, 5 g/L of sodium chloride and 2.5 g/L of $K_2HPO_4$) and incubated at 30° C. for 12 hours to 24 hours to obtain a liquid culture. In a 500 mL volume Erlenmeyer flask with baffle, 2 mL of the liquid culture is inoculated to 200 mL of a fresh TSB and cultured with shaking for 24 hours to 48 hours to obtain a liquid culture of the present bacterial strain (hereinafter referred to as Liquid Culture a). The Liquid Culture a is centrifuged according to a conventional manner to separate into a supernatant and precipitate. After removing the supernatant, the precipitate is washed with sterile water and centrifuged. The supernatant is removed to obtain bacterial cells of the present bacterial strain.

Preparation Example 4

The bacterial cells of the present bacterial strain obtained as described in Preparation Example 3 are suspended in water, dried on spray drier, and pulverized the resulting dried product to obtain a powder of the present bacterial strain.

Preparation Example 5

The Liquid Culture a is obtained as described in Preparation 3. The Liquid Culture a is frozen at −80° C., and freeze-dried and pulverized to obtain a powder of the present bacterial strain.

Preparation Example 6

In a Erlenmeyer flask with baffle, a platinum loop scraping of the present bacterial strain, which have been cultured in TSA (an agar medium containing 15 g/L of casein peptone, 5 g/L of soybean peptone, 5 g/L of sodium chloride, and 15 g/L of agar), were inoculated to a liquid medium containing 200 mL TSB (a liquid medium containing 17 g/L of casein peptone, 3 g/L of soybean peptone, 2.5 g/L of glucose, 5 g/L of sodium chloride and 2.5 g/L of $K_2HPO_4$) and incubated at 30° C. for 23 hours to obtain a liquid culture. The liquid culture (2% (v/v)) was inoculated to a fresh TSB in a Erlenmeyer flask with baffle and cultured at 30° C. with shaking for 43 hours to obtain a liquid culture of the present bacterial strain (hereinafter referred to as Liquid Culture b). The liquid culture b was centrifuged at 1900×g for 10 min to separate into a supernatant and a precipitate. After removing the supernatant, the precipitate was washed with sterilized water and centrifuged at 1900×g for 10 min. The supernatant was removed to obtain $3.8 \times 10^{11}$ cfu/g of bacterial cells of the present bacterial strain.

Preparation Example 7

The bacterial cells of the present bacterial strain obtained as described in Preparation Example 6 were frozen at −80° C. and freeze-dried. The dried product obtained thus by freeze-drying was pulverized using scoopula to obtain $2.8 \times 10^{12}$ cfu/g of a powder of the present bacterial strain.
Formulation Examples are provided below.

Formulation Example 1

To a mixture containing 0.2 parts of azoxystrobin, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 2

To a mixture containing 0.5 parts of pyraclostrobin, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 3

To a mixture containing 8.4 parts of picoxystrobin, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 4

To a mixture containing 0.4 parts of trifloxystrobin and 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 5

To a mixture containing 1 part of mandestrobin, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 6

To a mixture containing 2.6 parts of fluoxastrobin, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 7

To a mixture containing 5 parts of azoxystrobin and 30 parts of white carbon containing 30% by weight of polyoxyethylene alkyl ether sulfate ammonium salt are added the powder of the present bacterial strain obtained as described in Preparation Example 1 or 2, in an amount of $1 \times 10^{10}$ cfu per 1 g of the formulation, and water to 100 parts, followed by wet-milling to finely milled to obtain a flowable formulation.

Formulation Example 8

To a mixture containing 25 parts of pyraclostrobin and parts of white carbon containing 30% by weight of polyoxyethylene alkyl ether sulfate ammonium salt are added the powder of the present bacterial strain obtained as described in Preparation Example 1 or 2, in an amount of $1 \times 10^{10}$ cfu per 1 g of the formulation, and water to 100 parts, followed by wet-milling to finely milled to obtain a flowable formulation.

Formulation Example 9

To a mixture containing 42 parts of picoxystrobin and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 10

To a mixture containing 10 parts of trifloxystrobin and parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts are added and finely milled by wet-milling to obtain a flowable formulation.

Formulation Example 11

To a mixture containing 25 parts of mandestrobin and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 12

To a mixture containing 13 parts of fluoxastrobin and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 13

To a mixture containing 5 parts of white carbon, 8 parts of sodium lignin sulfonate, and 2 parts of sodium alkyl naphthalene sulfonate are added the bacterial cells or powder of the present bacterial strain obtained as described in any one of Preparation Examples 3 to 5, in an amount of $1\times10^{10}$ cfu per 1 g of the formulation, and diatomaceous earth to 100 parts to obtain a mixture. The mixture is milled to obtain wettable powder of the present bacterial strain.

Formulation Example 14

To 30 parts of white carbon containing 30% by weight of polyoxyethylene alkyl ether sulfate ammonium salt are added the bacterial cells or powder of the present bacterial strain obtained as described in any one of Preparation Examples 3 to 5, in an amount of $1\times10^{10}$ cfu or $1\times10^{12}$ cfu per 1 g of the formulation, and water to 100 parts to obtain a mixture. The mixture is finely milled by wet-milling to obtain a flowable formulation of the present bacterial strain.

Formulation Example 15

To a mixture containing 5 parts of white carbon, 8 parts of sodium lignin sulfonate, and 2 parts of sodium alkyl naphthalene sulfonate were added the powder of the present bacterial strain obtained in Preparation Example 7, in an amount of $1\times10^{10}$ cfu per 1 g of the formulation, and diatomaceous earth to 100 parts to obtain a mixture. The mixture was milled to obtain wettable powder of the present bacterial strain.

Formulation Example 16

To 30 parts of white carbon containing 30% by weight of polyoxyethylene alkyl ether sulfate ammonium salt were added the powder of the present bacterial strain obtained in Preparation Example 7, in an amount of $1\times10^{10}$ cfu or $1\times10^{12}$ cfu per 1 g of the formulation, and water to 100 parts to obtain a mixture. The mixture was finely milled by wet-milling to obtain a flowable formulation of the present bacterial strain.
Seed Treatment Examples are provided below.

Seed Treatment Example 1

To a mixture containing 5 parts of white carbon, 8 parts of sodium lignin sulfonate, and 2 parts of sodium alkyl naphthalene sulfonate are added the powder of the present bacterial strain obtained as described in Preparation Example 1, in an amount of $1\times10^{10}$ cfu per 1 g of the formulation, and diatomaceous earth to 100 parts, and the mixture was milled to obtain wettable powder of the present bacterial strain.

Corn seeds are treated by smearing treatment with 0.26 g of fluoxastrobin flowable formulation (41.4% flowable formulation, trade name: Fluoxastrobin ST, Bayer CropScience) per 1 kg of the seeds. The corn seeds thus treated with fluoxastrobin are treated by wet powder coating treatment with the wettable powder of the present bacterial strain in an amount of $1\times10^{10}$ cfu of the present bacterial strain per 1 kg of the seeds.

Seed Treatment Example 2

Soybean seeds are treated by smearing treatment with azoxystrobin flowable formulation (9.6% flowable formulation, trade name: Dynasty Syngenta Crop Protection LLC) in an amount of 0.02 g of azoxystrobin per 1 kg of the seeds. The soybean seeds thus treated with azoxystrobin are treated by wet powder coating treatment with the wettable powder of the present bacterial strain obtained as described in Seed Treatment Example 1 in an amount of $1\times10^{10}$ cfu of the present bacterial strain per 1 kg of the soybean seeds.

Seed Treatment Example 3

To 30 parts of white carbon containing 30% by weight of polyoxyethylene alkyl ether sulfate ammonium salt are added the powder of the present bacterial strain obtained as described in Preparation Example 2, in an amount of $1\times10^{10}$ cfu per 1 g of the formulation, and water to 100 parts, followed by wet-milling to finely milled to obtain a flowable formulation.

Corn seeds are treated by smearing treatment with a liquid mixture containing the flowable formulation of the present bacterial strain and pyraclostrobin flowable formulation (18.4% flowable formulation, trade name: Stamina Fungicide Seed Treatment, BASF), in an amount of $1\times10^{10}$ cfu of the present bacterial strain and 0.1 g of pyraclostrobin per 1 kg of the corn seeds.

Seed Treatment Example 4

Soybean seeds are treated by smearing treatment with a chemical liquid prepared by dissolving mandestrobin in acetone/Tween 20 (weight ratio=95:5) and diluting with water (adjusted to 0.1 g of mandestrobin per 1 kg of the seeds). The soybean seeds thus treated with mandestrobin are treated be smearing treatment with the flowable formulation of the present bacterial strain prepared as described in Seed Treatment Example 3 (adjusted to $1 \times 10^{10}$ cfu of the present bacterial strain per 1 kg of the seeds).

Seed Treatment Example 5

Corn seeds are treated by smearing treatment with the flowable formulation of the present bacterial strain and pyraclostrobin (adjusted to $2 \times 10^{10}$ cfu of the present bacterial strain and 0.1 g of pyraclostrobin per 1 kg of the seeds).

Seed Treatment Example 6

Soybean seeds are treated by smearing treatment with the flowable formulation of the present bacterial strain and picoxystrobin (adjusted to $2 \times 10^{10}$ cfu of the present bacterial and 0.84 g of picoxystrobin per 1 kg of the seeds).

Seed Treatment Example 7

Corn seeds are treated by smearing treatment with a mixture of the wettable powder of the present bacterial strain obtained in Formulation Example 13 and fluoxastrobin flowable formulation (41.4% flowable formulation, trade name: Fluoxastrobin ST, Bayer CropScience), in an amount of $1 \times 10^{10}$ cfu of the present bacterial strain and 0.26 g of fluoxastrobin per 1 kg of the seeds.

Seed Treatment Example 8

Corn seeds are treated by smearing treatment with a mixture of a flowable formulation of the present bacterial strain obtained in Formulation Example 14 and pyraclostrobin flowable formulation (18.4% flowable formulation, trade name: Stamina Fungicide Seed Treatment, BASF), in an amount of $1 \times 10^{10}$ cfu of the present bacterial strain and 0.1 g of pyraclostrobin per 1 kg of the seeds.

Test Examples are provided below.

Test Example 1

In a rotary seed treatment machine (trade name: HEGE11, manufactured by WINTERSTEIGER), corn seeds (variety: yellow dent corn) are treated by smearing treatment with a liquid mixture containing a flowable formulation of the present bacterial strain as prepared in Seed Treatment Example 3 (adjusted to $1 \times 10^{10}$ cfu per 1 kg of the corn seeds) and pyraclostrobin flowable formulation (18.4% flowable formulation, trade name: Stamina, BASF Corporation, adjusted to 0.1 g of pyraclostrobin per 1 kg of the corn seeds).

A plastic pot is filled with a soil, and then, the seeds thus treated are seeded and covered with a soil, which has been mixed with damping-off fungus (*Fusarium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Using untreated corn seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence(%)=100×(number of diseased plant/total number of seeded seeds):     Equation 1

Control value(%)=100×[(disease incidence in untreated compartment disease incidence in treated compartment)/disease incidence in untreated compartment]:     Equation 2

The composition of the invention shows a significantly higher controlling effect.

Test Example 2

In a rotary seed treatment machine (trade name: HEGE11, manufactured by WINTERSTEIGER), soybean seeds (variety: "Hatayutaka") are treated by smearing treatment with a liquid mixture containing a flowable formulation of the present bacterial strain obtained in the Seed Treatment Example 3 (adjusted to $1 \times 10^{10}$ cfu per 1 kg of the soybean seeds) and azoxystrobin flowable formulation (9.6% flowable formulation, trade name: Dynasty, Syngenta Crop Protection LLC, adjusted to 0.02 g of azoxystrobin per 1 kg of the soybean seeds).

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Using untreated soybean seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 3

Soybean seeds (variety: "Hatayutaka") are treated by wet powder coating treatment with the wettable powder of the present bacterial strain and azoxystrobin prepared in Formulation Example 1 (adjusted to $1 \times 10^{11}$ cfu of the present bacterial strain and 0.02 g of azoxystrobin per 1 kg of the soybean seeds), or with the wettable powder of the present bacterial strain and picoxystrobin prepared in Formulation Example 3 (adjusted to 1×10$^{11}$ cfu of the present bacterial strain and 0.84 g of picoxystrobin per 1 kg of the soybean seeds), or with the wettable powder of the present bacterial strain and trifloxystrobin prepared in Formulation Example 4 (adjusted to 1×10$^{11}$ cfu of the present bacterial strain and 0.04 g of trifloxystrobin per 1 kg of the soybean seeds), or with the wettable powder of the present bacterial strain and mandestrobin prepared in Formulation Example 5 (adjusted to 1×10$^{11}$ cfu of the present bacterial strain and 0.1 g of mandestrobin per 1 kg of the soybean seeds).

A plastic pot is filled with a soil, and then, the seeds thus treated are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Using untreated soybean seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 4

Corn seeds (variety: yellow dent corn) are treated by wet powder coating with the wettable powder of the present bacterial strain and pyraclostrobin prepared in Formulation Example 2 (adjusted to 1×10$^{11}$ cfu of the present bacterial strain and 0.1 g of pyraclostrobin per 1 kg of the corn seeds) or with the wettable powder of the present bacterial strain and fluoxastrobin prepared in Formulation Example 6 (adjusted to 1×10$^{11}$ cfu of the present bacterial strain and 0.26 g of fluoxastrobin per 1 kg of the corn seeds).

A plastic pot is filled with a soil, and then, the seeds thus treated are seeded and covered with a soil, which has been mixed with damping-off fungus (*Fusarium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Using untreated corn seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 5

In a rotary seed treatment machine (trade name: HEGE11, manufactured by WINTERSTEIGER), soybean seeds are treated by smearing treatment with the flowable formulation of the present bacterial strain and azoxystrobin prepared in Formulation Example 7 (adjusted to 2×10$^{10}$ cfu of the present bacterial strain and 0.02 g of azoxystrobin per 1 kg of the soybean seeds) or with the flowable formulation of the present bacterial strain and trifloxystrobin prepared in Formulation Example 10 (adjusted to 2×10$^{10}$ cfu of the present bacterial strain and 0.04 g of trifloxystrobin per 1 kg of the soybean seeds), or with the flowable formulation of the present bacterial strain and mandestrobin prepared in Formulation Example 11 (adjusted to 2×10$^{10}$ cfu of the present bacterial strain and 0.1 g of mandestrobin per 1 kg of the soybean seeds).

A plastic pot is filled with a soil, and then, the seeds thus treated are seeded and covered with a soil, which has been mixed with damping-off fungus (*Rhizoctonia solani*) cultured in a bran medium. Cultivation is carried out in a greenhouse under irrigation ("treated compartment"). The plants. are investigated 20 days after for the number of diseased plants, and the disease incidence is calculated by the following "Equation 1". Using untreated soybean seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment−disease incidence in treated compartment)/disease incidence in untreated compartment]: Equation 2

The composition of the invention shows a significantly higher controlling effect.

Test Example 6

In a rotary seed treatment machine (trade name: HEGE11, manufactured by WINTERSTEIGER), corn seeds are treated by smearing treatment with the flowable formulation of the present bacterial strain and pyraclostrobin prepared in Formulation Example 8 (adjusted to 2×10$^{10}$ cfu of the present bacterial strain and 0.1 g of pyraclostrobin per 1 kg of the corn seeds) or with the flowable formulation of the present bacterial strain and fluoxastrobin prepared in Formulation Example 12 (adjusted to $2\times10^{10}$ cfu of the present bacterial strain and 0.26 g of fluoxastrobin per 1 kg of the corn seeds).

A plastic pot is filled with a soil, and then, the treated seeds are seeded and covered with a soil, which has been mixed with damping-off fungus (*Fusarium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Using untreated corn seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 7

In a rotary seed treatment machine (trade name: HEGE11, manufactured by WINTERSTEIGER), soybean seeds are treated by smearing treatment with azoxystrobin flowable formulation (9.6% flowable formulation, trade name: Dynasty, Syngenta Crop Protection LLC, adjusted to 0.02 g of azoxystrobin per 1 kg of the seeds) or with trifloxystrobin flowable formulation (22% flowable formulation, trade name: TRILEX, Bayer CropScience, adjusted to 0.04 g of trifloxystrobin per 1 kg of the seeds), or with a chemical liquid prepared by dissolving picoxystrobin in acetone/Tween 20 (weight ratio=95:5) and diluting with water (adjusted to 0.84 g of picoxystrobin per 1 kg of the seeds), or with a chemical liquid prepared by dissolving mandestrobin in acetone/Tween 20 (weight ratio=95:5) and diluting with water (adjusted to 0.1 g of mandestrobin per 1 kg of the seeds). In a rotary seed treatment machine (trade name: HEGE11, manufactured by WINTERSTEIGER), the soybean seeds thus treated with azoxystrobin, trifloxystrobin, picoxystrobin or mandestrobin are treated by wet coating treatment with the wettable powder of the present bacterial strain obtained in Seed Treatment Example 1 (adjusted to $1\times10^{10}$ cfu of the present bacterial strain per 1 kg of the soybean seeds).

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Using untreated soybean seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 8

In a rotary seed treatment machine (trade name: HEGE11, manufactured by WINTERSTEIGER), corn seeds are treated by smearing treatment with pyraclostrobin flowable formulation (18.4% flowable formulation, trade name: Stamina, BASF Corporation, adjusted to 0.1 g of pyraclostrobin per 1 kg of the seeds) or with fluoxastrobin flowable formulation (41.4% flowable formulation, trade name: Fluoxastrobin ST, Bayer CropScience, adjusted to 0.26 g of fluoxastrobin per 1 kg of the seeds). In a rotary seed treatment machine (trade name: HEGE11, manufactured by WINTERSTEIGER), the soybean seeds thus treated with pyraclostrobin or fluoxastrobin are treated by wet coating treatment with the wettable powder of the present bacterial strain obtained in Seed Treatment Example 1 (adjusted to $1\times10^{10}$ cfu of the present bacterial strain per 1 kg of the corn seeds).

A plastic pot is filled with a soil, and then, the treated seeds are seeded and covered with a soil, which has been mixed with damping-off fungus (*Fusarium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Using untreated corn seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 9

In a rotary seed treatment machine (trade name: HEGE11, manufactured by WINTERSTEIGER), soybean seeds are treated by smearing treatment with the flowable formulation of the present bacterial strain obtained in Seed Treatment Example 3 in an amount of $1\times10^{10}$ cfu of the present bacterial strain per 1 kg of the soybean seeds. In a rotary seed treatment machine (trade name: HEGE11, manufactured by WINTERSTEIGER), the soybean seeds thus treated are treated by smearing treatment respectively with azoxystrobin flowable formulation (9.6% flowable formulation, trade name: Dynasty, Syngenta Crop Protection LLC, adjusted to 0.02 g of azoxystrobin per 1 kg of the seeds) or with trifloxystrobin flowable formulation (22% flowable formulation, trade name: TRILEX, Bayer CropScience, adjusted to 0.04 g of trifloxystrobin per 1 kg of the seeds), or with a chemical liquid prepared by dissolving picoxystrobin in acetone/Tween 20 (weight ratio=95:5) and diluting with water (adjusted to 0.84 g of picoxystrobin per 1 kg of the seeds), or with a chemical liquid prepared by dissolving mandestrobin in acetone/Tween 20 (weight ratio=95:5) and diluting with water (adjusted to 0.1 g of mandestrobin per 1 kg of the seeds).

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Using untreated soybean seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment−disease incidence in treated compartment)/disease incidence in untreated compartment]: Equation 2

The composition of the invention shows a significantly higher controlling effect.

Test Example 10

In a rotary seed treatment machine (trade name: HEGE11, manufactured by WINTERSTEIGER), corn seeds are treated by smearing treatment with the flowable formulation of the present bacterial strain obtained in Seed Treatment Example 3 in an amount of $1\times10^{10}$ cfu of the present bacterial strain per 1 kg of the seeds. In a rotary seed treatment machine (trade name: HEGE11, manufactured by WINTERSTEIGER), the corn seeds thus treated are treated by smearing treatment with a chemical liquid containing pyraclostrobin flowable formulation (18.4% flowable formulation, trade name: Stamina, BASF Corporation, adjusted to 0.1 g of pyraclostrobin per 1 kg of the seeds) or with fluoxastrobin flowable formulation (41.4% flowable formulation, trade name: Fluoxastrobin ST, Bayer CropScience, adjusted to 0.26 g of fluoxastrobin per 1 kg of the seeds).

A plastic pot is filled with a soil, and then, the treated seeds are seeded and covered with a soil, which has been mixed with damping-off fungus (*Fusarium solani*) cultured in a bran medium. Cultivation is carried out in a greenhouse under irrigation ("treated compartment"). The plants are investigated 20 days after for the number of diseased plants, and the disease incidence is calculated by the following "Equation 1". Using untreated corn seeds, seeding, covering with a soil and cultivation are conducted in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment−disease incidence in treated compartment)/disease incidence in untreated compartment]: Equation 2

The composition of the invention shows a significantly higher controlling effect.

Test Example 11

A chemical liquid is prepared by diluting azoxystrobin flowable formulation (20% flowable formulation, trade name: Amistar-20 FLOWABLE, Syngenta Japan) to 400 ppm of azoxystrobin, or by diluting pyraclostrobin wettable formulation (20% wettable granules, trade name: Calbio, BASF Japan) to 400 ppm of pyraclostrobin, or by diluting picoxystrobin in acetone/Tween 20 (weight ratio=95:5) and diluting with water to 400 ppm of picoxystrobin, or by diluting trifloxystrobin wettable formulation (25% flowable formulation, trade name: FLINT Flowable25, Bayer CropScience) to 400 ppm of trifloxystrobin, or by dissolving mandestrobin in acetone/Tween 20 (weight ratio=95:5) and diluting with water to 400 ppm of mandestrobin, or by dissolving fluoxastrobin in acetone/Tween 20 (weight ratio=95:5) and diluting with water to 400 ppm of fluoxastrobin, independently, and followed by combining the chemical liquid with the equal volume of a solution of the flowable formulation of the present bacterial strain obtained in Seed Treatment Example 1 (adjusted to $2\times10^8$ cfu of the present bacterial strain).

The chemical liquid is sprayed in a sufficient amount to pot planting barley (variety: two-row barley) wherein primary leaf development has occurred. After air drying, the plants are inoculated with barley net blotch fungus (*Pyrenophora teres Drechsler*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)] Equation The composition of the invention shows a significantly higher controlling effect.

Test Example 12

In a rotary seed treatment machine (trade name: HEGE11, manufactured by WINTERSTEIGER), corn seeds (variety:

yellow dent corn) are treated by smearing treatment using one of pyraclostrobin flowable formulation (18.4% flowable formulation, trade name: Stamina, BASF Corporation), fluoxastrobin flowable formulation (41.4% flowable formulation, trade name: Fluoxastrobin ST, Bayer CropScience), the wettable powder of the present bacterial strain obtained in Formulation Example 13, and the flowable formulation of the present bacterial strain obtained in Formulation Example 14, so that the corn seeds retain the present bacterial strain and the compound in the amount shown in Table 1.

A plastic pot is filled with a soil, and then, the coon seeds, which have been treated with the present bacterial strain, compound or the present bacterial strain+compound as shown in Table 1, are seeded and covered with a soil, which has been mixed with damping-off fungus (*Fusarium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Similar procedures are conducted using untreated corn seeds, instead of the treated corn seeds, as described above for the treated compartment ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The compartment treated with the composition of the invention shows a synergistic controlling effect, for each combination of the present bacterial strain and the compound, compared with that of the corresponding compartment treated solely with the present bacterial strain or the compound.

TABLE 1

| Bacteria/Compound retained by Seeds | Retaining Amount (/Kg seeds) |
|---|---|
| The present bacterial strain | $1 \times 10^{10}$ cfu |
| The present bacterial strain | $1 \times 10^{8}$ cfu |
| The present bacterial strain | $1 \times 10^{7}$ cfu |
| pyraclostrobin | 0.025 g |
| pyraclostrobin | 0.05 g |
| pyraclostrobin | 0.1 g |
| fluoxastrobin | 0.05 g |
| fluoxastrobin | 0.1 g |
| fluoxastrobin | 0.2 g |
| The present bacterial strain | $1 \times 10^{10}$ cfu |
| pyraclostrobin | 0.025 g |
| The present bacterial strain | $1 \times 10^{10}$ cfu |
| pyraclostrobin | 0.05 g |
| The present bacterial strain | $1 \times 10^{10}$ cfu |
| pyraclostrobin | 0.1 g |
| The present bacterial strain | $1 \times 10^{10}$ cfu |
| fluoxastrobin | 0.05 g |
| The present bacterial strain | $1 \times 10^{10}$ cfu |
| fluoxastrobin | 0.1 g |
| The present bacterial strain | $1 \times 10^{10}$ cfu |
| fluoxastrobin | 0.2 g |

TABLE 1-continued

| Bacteria/Compound retained by Seeds | Retaining Amount (/Kg seeds) |
|---|---|
| The present bacterial strain | $1 \times 10^{7}$ cfu |
| pyraclostrobin | 0.025 g |
| The present bacterial strain | $1 \times 10^{7}$ cfu |
| pyraclostrobin | 0.05 g |
| The present bacterial strain | $1 \times 10^{7}$ cfu |
| pyraclostrobin | 0.1 g |
| The present bacterial strain | $1 \times 10^{8}$ cfu |
| fluoxastrobin | 0.05 g |
| The present bacterial strain | $1 \times 10^{8}$ cfu |
| fluoxastrobin | 0.1 g |
| The present bacterial strain | $1 \times 10^{8}$ cfu |
| fluoxastrobin | 0.2 g |

Test Example 13

In a rotary seed treatment machine (trade name: HEGE11, manufactured by WINTERSTEIGER), soybean seeds (variety: "Hatayutaka") are treated by smearing treatment using azoxystrobin flowable formulation (9.6% flowable formulation, trade name: Dynasty Syngenta Crop Protection LLC), trifloxystrobin flowable formulation (22% flowable formulation, trade name: TRILEX, Bayer CropScience), a chemical liquid prepared by dissolving picoxystrobin in acetone/Tween 20 (weight ratio=95:5) and diluting with water, a chemical liquid prepared by dissolving mandestrobin in acetone/Tween 20 (weight ratio=95:5) and diluting with water, and the wettable powder of the present bacterial strain obtained in Formulation Example 13, or the flowable formulation of the present bacterial strain obtained in Formulation Example 14, so that the soybean seeds retain the bacteria and the compound in the amount shown in Table 2.

A plastic pot is filled with a soil, which has been mixed with damping-off fungus (*Rhizoctonia solani*) cultured in a bran medium, and then, the soybean seeds, which have been treated with the present bacterial strain, compound or the present bacterial strain+compound as shown in Table 2, are seeded and covered with a soil ("treated compartment"). Cultivation is carried out in a greenhouse under irrigation. The plants are investigated 20 days after for the number of diseased plants, and the disease incidence is calculated by the following "Equation 1". Similar procedures are conducted using untreated soybean seeds, instead of the treated soybean seeds, as described above for the treated compartment ("untreated compartment").

The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The compartment treated with the composition of the invention shows a synergistic controlling effect, for each combination of the present bacterial strain and the compound, compared with that of the corresponding compartment treated solely with the present bacterial strain or the compound.

TABLE 2

| Bacteria/Compound retained by Seeds | Retaining Amount (/Kg seeds) |
|---|---|
| The present bacterial strain | $1 \times 10^{10}$ cfu |
| The present bacterial strain | $1 \times 10^{12}$ cfu |
| The present bacterial strain | $1 \times 10^{7}$ cfu |
| Azoxystrobin | 0.005 g |
| Azoxystrobin | 0.01 g |
| Azoxystrobin | 0.02 g |
| Trifloxystrobin | 0.002 g |
| Trifloxystrobin | 0.01 g |
| Trifloxystrobin | 0.05 g |
| Picoxystrobin | 0.002 g |
| Picoxystrobin | 0.01 g |
| Picoxystrobin | 0.05 g |
| Mandestrobin | 0.025 g |
| Mandestrobin | 0.05 g |
| Mandestrobin | 0.1 g |
| The present bacterial strain | $1 \times 10^{10}$ cfu |
| Azoxystrobin | 0.005 g |
| The present bacterial strain | $1 \times 10^{10}$ cfu |
| Azoxystrobin | 0.01 g |
| The present bacterial strain | $1 \times 10^{10}$ cfu |
| Azoxystrobin | 0.02 g |
| The present bacterial strain | $1 \times 10^{10}$ cfu |
| Trifloxystrobin | 0.002 g |
| The present bacterial strain | $1 \times 10^{10}$ cfu |
| Trifloxystrobin | 0.01 g |
| The present bacterial strain | $1 \times 10^{10}$ cfu |
| Trifloxystrobin | 0.05 g |
| The present bacterial strain | $1 \times 10^{10}$ cfu |
| Picoxystrobin | 0.002 g |
| The present bacterial strain | $1 \times 10^{10}$ cfu |
| Picoxystrobin | 0.01 g |
| The present bacterial strain | $1 \times 10^{10}$ cfu |
| Picoxystrobin | 0.05 g |
| The present bacterial strain | $1 \times 10^{10}$ cfu |
| Mandestrobin | 0.025 g |
| The present bacterial strain | $1 \times 10^{10}$ cfu |
| Mandestrobin | 0.05 g |
| The present bacterial strain | $1 \times 10^{10}$ cfu |
| Mandestrobin | 0.1 g |
| The present bacterial strain | $1 \times 10^{12}$ cfu |
| Azoxystrobin | 0.005 g |
| The present bacterial strain | $1 \times 10^{12}$ cfu |
| Azoxystrobin | 0.01 g |
| The present bacterial strain | $1 \times 10^{12}$ cfu |
| Azoxystrobin | 0.02 g |
| The present bacterial strain | $1 \times 10^{12}$ cfu |
| Trifloxystrobin | 0.002 g |
| The present bacterial strain | $1 \times 10^{12}$ cfu |
| Trifloxystrobin | 0.01 g |
| The present bacterial strain | $1 \times 10^{12}$ cfu |
| Trifloxystrobin | 0.05 g |
| The present bacterial strain | $1 \times 10^{12}$ cfu |
| Picoxystrobin | 0.002 g |
| The present bacterial strain | $1 \times 10^{12}$ cfu |
| Picoxystrobin | 0.01 g |
| The present bacterial strain | $1 \times 10^{12}$ cfu |
| Picoxystrobin | 0.05 g |
| The present bacterial strain | $1 \times 10^{7}$ cfu |
| Mandestrobin | 0.025 g |
| The present bacterial strain | $1 \times 10^{7}$ cfu |
| Mandestrobin | 0.05 g |
| The present bacterial strain | $1 \times 10^{7}$ cfu |
| Mandestrobin | 0.1 g |

Test Example 14

Spray liquids are prepared and adjusted their concentrations as shown in Table 3, respectively, for a flowable powder of the present bacterial strain as obtained in Formulation Example 13, azoxystrobin flowable formulation (20% flowable formulation, trade name: Amistar FLOWABLE 20, Syngenta Japan), pyraclostrobin wettable formulation (20% wettable granules, trade name: Calbio, BASF Japan), a chemical liquid prepared by diluting picoxystrobin in acetone/Tween 20 (weight ratio=95:5) and diluting with water, trifloxystrobin wettable formulation (25% flowable formulation, trade name: FLINT Flowable25, Bayer CropScience), a chemical liquid prepared by dissolving mandestrobin in acetone/Tween 20 (weight ratio=95:5) and diluting with water, and a chemical liquid prepared by dissolving fluoxastrobin in acetone/Tween 20 (weight ratio=95:5) and diluting with water.

The liquid (50 mL) is sprayed to pot planting barley (variety: two-row barley) wherein primary leaf development has occurred. After air drying, the plants are inoculated with barley net blotch fungus (*Pyrenophora teres Drechsler*) and left to stand under moisture condition for 10 days ("treated compartment"). Also, similar procedures are conducted without spraying the liquid ("untreated compartment").

The effect on the treated compartment is determined by the following equation, based on the onset area rates of the treated compartment and the untreated compartment.

$$\text{controlling effect} = 100 \times [1 - (\text{onset area rate of treated compartment})/(\text{onset area rate of untreated compartment})] \quad \text{Equation}$$

The compartment treated with the composition of the invention shows a synergistic controlling effect, for each combination of the present bacterial strain and the compound, compared with that of the corresponding compartment treated solely with the present bacterial strain or the compound.

TABLE 3

| Bacteria/Compound sprayed to plants | Amount of Bacteria/Compound in Spray Liquid (/L) |
|---|---|
| The present bacterial strain | $1 \times 10^{8}$ cfu |
| Azoxystrobin | 0.2 mg |
| Azoxystrobin | 0.4 mg |
| Trifloxystrobin | 0.2 mg |
| Trifloxystrobin | 0.4 mg |
| Picoxystrobin | 0.1 mg |
| Picoxystrobin | 0.2 mg |
| Mandestrobin | 0.2 mg |
| Mandestrobin | 0.4 mg |
| Pyraclostrobin | 0.1 mg |
| Pyraclostrobin | 0.2 mg |
| Fluoxastrobin | 0.2 mg |
| Fluoxastrobin | 0.4 mg |
| The present bacterial strain | $1 \times 10^{8}$ cfu |
| Azoxystrobin | 0.2 mg |
| The present bacterial strain | $1 \times 10^{8}$ cfu |
| Azoxystrobin | 0.4 mg |
| The present bacterial strain | $1 \times 10^{8}$ cfu |
| Trifloxystrobin | 0.2 mg |
| The present bacterial strain | $1 \times 10^{8}$ cfu |
| Trifloxystrobin | 0.4 mg |
| The present bacterial strain | $1 \times 10^{8}$ cfu |
| Picoxystrobin | 0.1 mg |
| The present bacterial strain | $1 \times 10^{8}$ cfu |
| Picoxystrobin | 0.2 mg |
| The present bacterial strain | $1 \times 10^{8}$ cfu |
| Mandestrobin | 0.2 mg |
| The present bacterial strain | $1 \times 10^{8}$ cfu |
| Mandestrobin | 0.4 mg |
| The present bacterial strain | $1 \times 10^{8}$ cfu |
| Pyraclostrobin | 0.1 mg |
| The present bacterial strain | $1 \times 10^{8}$ cfu |
| Pyraclostrobin | 0.2 mg |
| The present bacterial strain | $1 \times 10^{8}$ cfu |
| Fluoxastrobin | 0.2 mg |
| The present bacterial strain | $1 \times 10^{8}$ cfu |
| Fluoxastrobin | 0.4 mg |

Test Example 15

In a rotary seed treatment machine (trade name: HEGE11, manufactured by WINTERSTEIGER), corn seeds (variety:

yellow dent corn) were treated by smearing treatment using pyraclostrobin flowable formulation (20% wettable granules, trade name: Comet, BASF. Corporation), a chemical liquid prepared by dissolving fluoxastrobin in acetone/Tween 20 (weight ratio=95:5) and diluting with water, and the flowable formulation of the present bacterial strain obtained in Formulation Example 16, respectively, so that the corn seeds retain the present bacterial strain and the compound in the amount shown in Table 4.

A plastic pot was filled with a soil, and then, the coon seeds, which have been treated with the present bacterial strain, compound or the present bacterial strain+compound as shown in Table 4, were seeded and covered with a soil, which has been mixed with damping-off fungus (*Fusarium* spp.) cultured in a bran medium ("treated compartment"). Cultivation was carried out in a greenhouse under irrigation. Also, similar procedures were conducted using untreated corn seeds, instead of the treated corn seeds, as described above for the treated compartment ("untreated compartment"). The plants were investigated 20 days after for the number of diseased plants, and the disease incidence was calculated by the following "Equation 1". The control value of the treated compartment was calculated by the following equation "Equation 2", based on the disease incidences of the treated compartment and the untreated compartment.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

TABLE 4

| Bacteria/Compound retained by Seeds | Retaining Amount (/Kg seeds) | Controlling Effect | Estimated Value* |
|---|---|---|---|
| The present bacterial strain | 1 × 10$^{10}$ cfu | 11.6 | — |
| The present bacterial strain | 1 × 10$^{8}$ cfu | 7.0 | — |
| The present bacterial strain | 1 × 10$^{7}$ cfu | 4.7 | — |
| Pyraclostrobin | 0.025 g | 18.6 | — |
| Pyraclostrobin | 0.05 g | 25.6 | — |
| Pyraclostrobin | 0.1 g | 37.2 | — |
| Fluoxastrobin | 0.05 g | 14.0 | — |
| Fluoxastrobin | 0.1 g | 30.2 | — |
| Fluoxastrobin | 0.2 g | 41.9 | — |
| The present bacterial strain | 1 × 10$^{10}$ cfu | 34.9 | 28.1 |
| Pyraclostrobin | 0.025 g | | |
| The present bacterial strain | 1 × 10$^{10}$ cfu | 44.2 | 34.3 |
| Pyraclostrobin | 0.05 g | | |
| The present bacterial strain | 1 × 10$^{10}$ cfu | 55.8 | 44.5 |
| Pyraclostrobin | 0.1 g | | |
| The present bacterial strain | 1 × 10$^{10}$ cfu | 32.6 | 24.0 |
| Fluoxastrobin | 0.05 g | | |
| The present bacterial strain | 1 × 10$^{10}$ cfu | 51.2 | 38.3 |
| Fluoxastrobin | 0.1 g | | |
| The present bacterial strain | 1 × 10$^{10}$ cfu | 67.4 | 48.7 |
| Fluoxastrobin | 0.2 g | | |
| The present bacterial strain | 1 × 10$^{7}$ cfu | 32.6 | 22.4 |
| Pyraclostrobin | 0.025 g | | |
| The present bacterial strain | 1 × 10$^{7}$ cfu | 41.9 | 29.0 |
| Pyraclostrobin | 0.05 g | | |
| The present bacterial strain | 1 × 10$^{7}$ cfu | 53.5 | 40.1 |
| Pyraclostrobin | 0.1 g | | |
| The present bacterial strain | 1 × 10$^{8}$ cfu | 30.2 | 20.0 |
| Fluoxastrobin | 0.05 g | | |
| The present bacterial strain | 1 × 10$^{8}$ cfu | 44.2 | 35.1 |
| Fluoxastrobin | 0.1 g | | |
| The present bacterial strain | 1 × 10$^{8}$ cfu | 60.5 | 46.0 |
| Fluoxastrobin | 0.2 g | | |

*Control value estimated from the calculation by the Colby's equation

If the effect by the combination of two active ingredients is greater than that of the estimated value E, which is calculated by the Colby's equation as follows, the effect is regarded as synergistic.

$$E = X + Y - X \cdot Y / 100$$

wherein,
E=Control value when using the mixture of the active ingredients A and B at the concentrations m and n (amount of the active ingredient), respectively.
X=Control value when using the active ingredient A at the concentration m (amount of the active ingredient).
Y=Control value when using the active ingredient B at the concentration n (amount of the active ingredient).

The compartment treated with the composition of the invention showed a synergistic controlling effect, for each combination of the present bacterial strain and the compound, compared with that of the corresponding compartment treated solely with the present bacterial strain or the compound.

Test Example 16

In a rotary seed treatment machine (trade name: HEGE11, manufactured by WINTERSTEIGER), soybean seeds (variety:"Hatayutaka") were treated by smearing treatment using azoxystrobin flowable formulation (25% flowable formulation, trade name: Amistar, Syngenta), trifloxystrobin flowable formulation (25% flowable formulation, trade name: FLINT, Bayer CropScience), a chemical liquid prepared by diluting picoxystrobin in acetone/Tween 20 (weight ratio=95:5) and diluting with water, a chemical liquid prepared by dissolving mandestrobin in acetone/Tween 20 (weight ratio=95:5) and diluting with water, and the flowable formulation obtained of the present bacterial strain in Formulation Example 16, so that the soybean seeds retain the bacteria and the compound in the amount shown in Table 5.

A plastic pot was filled with a soil, which has been mixed with damping-off fungus (*Rhizoctonia solani*), and then, the soybean seeds, which have been treated with the present bacterial strain, compound or the present bacterial strain+compound as shown in Table 5, were seeded and covered with a soil ("treated compartment"). Cultivation was carried out in a greenhouse under irrigation. Also, similar procedures were conducted using untreated soybean seeds, instead of the treated soybean seeds, as described above for the treated compartment ("untreated compartment"). The plants were investigated 20 days after for the number of diseased plants, and the disease incidence was calculated by the following "Equation 1". The control value of the treated compartment was calculated by the following equation "Equation 2", based on the disease incidences of the treated compartment and the untreated compartment.

Disease incidence (%)=100×(number of diseased plant/total number of seeded seeds):  Equation 1

Control value (%)=100×[(disease incidence in untreated compartment−disease incidence in treated compartment)/disease incidence in untreated compartment]:  Equation 2

TABLE 5

| Bacteria/Compound retained by Seeds | Retaining Amount (/Kg seeds) | Controlling Effect | Estimated Value* |
|---|---|---|---|
| The present bacterial strain | 1 × 10$^{10}$ cfu | 11.4 | — |
| The present bacterial strain | 1 × 10$^{12}$ cfu | 18.2 | — |
| The present bacterial strain | 1 × 10$^{7}$ cfu | 4.6 | — |
| Azoxystrobin | 0.005 g | 15.9 | — |
| Azoxystrobin | 0.01 g | 29.5 | — |
| Azoxystrobin | 0.02 g | 38.6 | — |
| Trifloxystrobin | 0.002 g | 20.5 | — |
| Trifloxystrobin | 0.01 g | 31.8 | — |
| Trifloxystrobin | 0.05 g | 40.9 | — |
| Picoxystrobin | 0.002 g | 18.2 | — |
| Picoxystrobin | 0.01 g | 27.3 | — |
| Picoxystrobin | 0.05 g | 38.6 | — |
| Mandestrobin | 0.025 g | 25.0 | — |
| Mandestrobin | 0.05 g | 36.4 | — |
| Mandestrobin | 0.1 g | 47.7 | — |
| The present bacterial strain Azoxystrobin | 1 × 10$^{10}$ cfu 0.005 g | 31.8 | 25.5 |
| The present bacterial strain Azoxystrobin | 1 × 10$^{10}$ cfu 0.01 g | 45.5 | 37.5 |
| The present bacterial strain Azoxystrobin | 1 × 10$^{10}$ cfu 0.02 g | 63.6 | 45.6 |
| The present bacterial strain Trifloxystrobin | 1 × 10$^{10}$ cfu 0.002 g | 38.6 | 29.5 |
| The present bacterial strain Trifloxystrobin | 1 × 10$^{10}$ cfu 0.01 g | 54.6 | 39.6 |
| The present bacterial strain Trifloxystrobin | 1 × 10$^{10}$ cfu 0.05 g | 70.5 | 47.6 |
| The present bacterial strain Picoxystrobin | 1 × 10$^{10}$ cfu 0.002 g | 34.1 | 27.5 |
| The present bacterial strain Picoxystrobin | 1 × 10$^{10}$ cfu 0.01 g | 43.2 | 35.5 |
| The present bacterial strain Picoxystrobin | 1 × 10$^{10}$ cfu 0.05 g | 68.2 | 45.6 |
| The present bacterial strain Mandestrobin | 1 × 10$^{10}$ cfu 0.025 g | 45.5 | 33.5 |
| The present bacterial strain Mandestrobin | 1 × 10$^{10}$ cfu 0.05 g | 56.8 | 43.6 |
| The present bacterial strain Mandestrobin | 1 × 10$^{10}$ cfu 0.1 g | 75.0 | 53.7 |
| The present bacterial strain Azoxystrobin | 1 × 10$^{12}$ cfu 0.005 g | 40.9 | 31.2 |
| The present bacterial strain Azoxystrobin | 1 × 10$^{12}$ cfu 0.01 g | 52.3 | 42.3 |
| The present bacterial strain Azoxystrobin | 1 × 10$^{12}$ cfu 0.02 g | 72.7 | 49.8 |
| The present bacterial strain Trifloxystrobin | 1 × 10$^{12}$ cfu 0.002 g | 43.2 | 34.9 |
| The present bacterial strain Trifloxystrobin | 1 × 10$^{12}$ cfu 0.01 g | 54.6 | 44.2 |
| The present bacterial strain Trifloxystrobin | 1 × 10$^{12}$ cfu 0.05 g | 77.3 | 51.7 |
| The present bacterial strain Picoxystrobin | 1 × 10$^{12}$ cfu 0.002 g | 36.4 | 33.1 |
| The present bacterial strain Picoxystrobin | 1 × 10$^{12}$ cfu 0.01 g | 54.6 | 40.5 |
| The present bacterial strain Picoxystrobin | 1 × 10$^{12}$ cfu 0.05 g | 75.0 | 49.8 |
| The present bacterial strain Mandestrobin | 1 × 10$^{7}$ cfu 0.025 g | 40.9 | 28.4 |
| The present bacterial strain Mandestrobin | 1 × 10$^{7}$ cfu 0.05 g | 50.0 | 39.3 |
| The present bacterial strain Mandestrobin | 1 × 10$^{7}$ cfu 0.1 g | 70.5 | 50.1 |

*Control value estimated from the calculation by the Colby's equation

The compartment treated with the composition of the invention showed a synergistic controlling effect, for each combination of the present bacterial strain and the compound, compared with that of the corresponding compartment treated solely with the present bacterial strain or the compound.

The invention claimed is:

1. A composition for control plant diseases comprising *Bacillus* strain APM-1 deposited under ATCC Accession No. PTA-4838 and one or more ubiquinol oxidase Qo site inhibitor,
   wherein the composition comprises the ubiquinol oxidase Qo site inhibitor in an amount of $10^{-5}$ to $10^2$ g per $10^{10}$ cfu of *Bacillus* strain APM-1.

2. The composition according to claim 1 wherein the ubiquinol oxidase Qo site inhibitor is selected from the group consisting of azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin.

3. A plant seed or a vegetative propagation organ comprising $10^6$ to $10^{13}$ cfu of *Bacillus* strain APM-1 deposited under ATCC Accession No. PTA-4838 and 0.0001 to 10 g of one or more ubiquinol oxidase Qo site inhibitor, per 1 kg of the seed or vegetative propagation organ.

4. The plant seed or a vegetative propagation organ according to claim 3 wherein the ubiquinol oxidase Qo site inhibitor is selected from the group consisting of azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin.

5. A plant seed or a vegetative propagation organ according to claim 3, wherein the plant seed or the vegetative propagation organ comprises $10^7$ to $10^{12}$ cfu of *Bacillus* strain APM-1 deposited under ATCC Accession No. PTA-4838 and 0.002 to 0.2 g of one or more ubiquinol oxidase Qo site inhibitor, per 1 kg of the seed or vegetative propagation organ.

6. The plant seed or a vegetative propagation organ according to claim 5 wherein the ubiquinol oxidase Qo site inhibitor is selected from the group consisting of azoxystrobin, mandestrobin, pyraclostrobin, kresoxim-methyl, trifloxystrobin, metominostrobin, orysastrobin, famoxadone, fenamidon, pyribencarb, picoxystrobin, and fluoxastrobin.

7. A method for controlling plant diseases, comprising a step of applying *Bacillus* strain APM-1 deposited under ATCC Accession No. PTA-4838 and one or more ubiquinol oxidase Qo site inhibitor to a plant or a plant cultivation site,
   wherein the ubiquinol oxidase Qo site inhibitor is applied in an amount of $10^{-5}$ to $10^2$ g per $10^{10}$ cfu of *Bacillus* strain APM-1.

8. The method for controlling plant diseases according to claim 7 wherein the plant is a genetically modified plant.

* * * * *